US011317633B2

(12) United States Patent
Ferreira et al.

(10) Patent No.: US 11,317,633 B2
(45) Date of Patent: May 3, 2022

(54) MICROBIAL COMPOSITIONS AND METHODS

(71) Applicant: MONSANTO TECHNOLOGY, LLC, St. Louis, MO (US)

(72) Inventors: Kenneth L. Ferreira, Wentzville, MO (US); Linda L. Lutfiyya, St. Louis, MO (US); Ryan T. McCann, San Diego, CA (US); Scott R. Schaecher, Webster Groves, MO (US)

(73) Assignee: MONSANTO TECHNOLOGY, LLC, St. Louis, MO (US)

( * ) Notice: Subject to any disclaimer, the term of this patent is extended or adjusted under 35 U.S.C. 154(b) by 260 days.

(21) Appl. No.: 16/475,631

(22) PCT Filed: Jan. 2, 2018

(86) PCT No.: PCT/US2018/012084
§ 371 (c)(1),
(2) Date: Jul. 2, 2019

(87) PCT Pub. No.: WO2018/128986
PCT Pub. Date: Jul. 12, 2018

(65) Prior Publication Data
US 2019/0320662 A1 Oct. 24, 2019

Related U.S. Application Data

(60) Provisional application No. 62/573,071, filed on Oct. 16, 2017, provisional application No. 62/449,981, filed on Jan. 24, 2017, provisional application No. 62/441,929, filed on Jan. 3, 2017.

(51) Int. Cl.
| | |
|---|---|
| *A01N 63/22* | (2020.01) |
| *A01C 1/06* | (2006.01) |
| *C12N 1/20* | (2006.01) |
| *A01N 25/04* | (2006.01) |
| *C12R 1/07* | (2006.01) |

(52) U.S. Cl.
CPC ............... *A01N 63/22* (2020.01); *A01C 1/06* (2013.01); *C12N 1/205* (2021.05); *A01N 25/04* (2013.01); *C12R 2001/07* (2021.05)

(58) Field of Classification Search
CPC ....... C12N 1/205; A01C 1/06; C12R 2001/07; A01N 63/22; A01N 25/04
See application file for complete search history.

(56) References Cited

U.S. PATENT DOCUMENTS

| | | | |
|---|---|---|---|
| 4,465,017 A | 8/1984 | Simmons | |
| 4,759,945 A | 7/1988 | Nemecek et al. | |
| 5,080,925 A | 1/1992 | Kouno | |
| 5,107,787 A | 4/1992 | Kuono | |
| 5,389,399 A | 2/1995 | Bazin et al. | |
| 5,549,718 A | 8/1996 | Lerouge et al. | |
| 5,554,445 A | 9/1996 | Struszczyk et al. | |
| 5,891,246 A | 4/1999 | Lund | |
| 5,918,413 A | 7/1999 | Otani et al. | |
| 9,615,583 B2 | 4/2017 | Kloepper et al. | |
| 9,688,730 B2 | 6/2017 | Cerf et al. | |
| 2005/0260619 A1 | 11/2005 | Brousseau et al. | |
| 2010/0193752 A1* | 8/2010 | Phelps et al. ............ | 252/519.4 |
| 2012/0231951 A1 | 9/2012 | Guilhabert-Goya et al. | |
| 2014/0007292 A1 | 1/2014 | Cerf et al. | |
| 2016/0192661 A1 | 7/2016 | Kloepper et al. | |
| 2016/0289130 A1 | 10/2016 | Innes et al. | |

FOREIGN PATENT DOCUMENTS

| | | |
|---|---|---|
| CN | 102174430 | 9/2011 |
| CN | 103281905 | 9/2013 |
| EP | 2654433 A1 | 10/2013 |

OTHER PUBLICATIONS

GenBank Accession No. AB576891.1, dated Aug. 24, 2010.
Williamson et al., "Optimizing the indirect extraction of prokaryotic DNA from soils", Soil Biology and Chemistry, 43(4):736-748, Apr. 29, 2010.
GenBank Accession No. AB576892.1, Aug. 24, 2010.
Extended European Search Report regarding EP Application No. 18736464.1 dated May 28, 2020.
International Search Report and Written Opinion for PCT/US2018/012084, dated Apr. 13, 2018.
"AB576893: *Bacillus* sp. DSL09-2 gene for 16S rRNA," NCBI GenBank Accession No. AB576893.1, Aug. 24, 2010, p. 1; retrieved from the internet: www.ncbi.nim.nih.aov/nuccore/AB576893 on Mar. 7, 2019.
Goto et al., "Application of the partial 16S rDNA sequence as an index for rapid identification of species in the genus *Bacillus*," *J of General and Applied Microbiology*, vol. 46, No. pp. 1-8; Feb. 28, 2000.
Yadav et al. "Prospecting cold deserts of northwestern Himalayas for microbial diversity and plant growth promoting attributes," *J of Bioscience and Bioengineering*; vol. 119, No. 6, pp. 683-693; Jan. 6, 2015.
Burges, Formulation of Microbial Biopesticides, Beneficial Microorganisms, Nematodes and Seed Treatments, Book, (2012), 412 pages, Springer Science & Business Media, Dordrecht.
D'Haeze, et al., "Nod Factor Structures, Responses, and Perception during Initiation of Nodule Development," Glycobiology, (2002), 79R-105R, 12(6).

(Continued)

*Primary Examiner* — Satyendra K Singh
(74) *Attorney, Agent, or Firm* — Dentons US LLP; David Lanzotti

(57) ABSTRACT

Microbial compositions for application to plants, plant parts and plant seeds are provided for improvement of plant yield and/or other beneficial plant traits. Methods of making and applying microbial compositions or formulations to plants, plant parts or plant seeds or to growth media are further provided to increase or improve plant yield and/or other beneficial plant traits.

17 Claims, No Drawings
Specification includes a Sequence Listing.

(56) References Cited

OTHER PUBLICATIONS

Defaria and Wraight, "Mycoinsecticides and Mycoacaricides: A comprehensive list with worldwide coverage and international classification of formulation types," Biological Control, (2007), 237-256, 43(3).
Demont-Caulet, et al., "Nodule-Inducing Activity of Synthetic Sinorhizobium meliloti Nodulation Factors and Related Lipo-Chitooligosaccharides on Alfalfa. Importance of the Acyl Chain Structure," Plant Physiology, (1999), 83-92, 120(1).
Denarie, et al., "Rhizobium Lipo-Chitooligosaccharide Nodulation Factors: Signaling Molecules Mediating Recognition and Morphogenesis," Annual Review of Biochemistry, (1996), 503-535, 65(1).
Diaz, et al., "Heterologous Rhizobial Lipochitin Oligosaccharides and Chitin Oligomers Induce Cortical Cell Divisions in Red Clover Roots, Transformed with the Pea Lectin Gene," Molecular Plant Microbe Interactions, (2000), 268-276, 13(3).
Hamel and Beaudoin, "Chitooligosaccharide Sensing and Downstream Signaling: Contrasted Outcomes in Pathogenic and Beneficial Plant-Microbe Interactions," Planta, (2010), 787-806, 232(4).
Hungria and Stacey, "Molecular Signals Exchanged Between Host Plants and Rhizobia: Basic Aspects and Potential Application in Agriculture," Soil Biology and Biochemistry, (1997), 819-830, 29(5-6).
Mabood, et al., "Jasmonates Induce Nod Factor Production by Bradyrhizobium Japonicum," Plant Physiology and Biochemistry, (2006), 759-65, 44(11-12).
Mabood, et al., "Bradyrhizobium Japonicum Preincubated with Methyl Jasmonate Increases Soybean Nodulation and Nitrogen Fixation," Agronomy Journal, (2006), 289-294, 98(2).
Mabood, et al., "Methyl Jasmonate, Alone or in Combination with Genistein, and Bradyrhizobium Japonicum Increases Soybean (*Glycine max* L.) Plant Dry Matter Production and Grain Yield Under Short Season Conditions," Field Crops Research, (2006), 412-419, 95(2-3).
Müller, et al., "Nod Factors and Chitooligomers Elicit an Increase in Cytosolic Calcium in Aequorin-Expressing Soybean Cells," Plant Physiology, (2000), 733-740, 124(2).
Premachandra, et al., "Bacterial Modes of Action for Enhancing of Plant Growth," Journal of Biotechnology & Biomaterials, (2016), 1-8, 6(3).
Prome, et al., "Acylated Chitooligomers are Molecular Signals that Mediate the Symbiotic Interactions Between Nitrogen-Fixing Bacteria and Their Host Plants," Pure and Applied Chemistry, (1998), 55-60, 70(1).
Puoci, et al., "Polymer in Agriculture: a Review." American Journal of Agricultural and Biological Sciences, (2008), 299-314, 3(1).
Robina, et al., "Synthesis and Biological Evaluation of Oligosaccharides Related to the Molecule Signals in Plant Defence and the Rhizobium-Legume Symbiosis," Tetrahedron, (2002), 521-530, 58(3).
Rouge, et al., "Docking of Chitin Oligomers and Nod Factors on Lectin Domains of the LysM-RLK Receptors in the Medicago-Rhizobium Symbiosis," The Molecular Immunology of Complex Carbohydrates-3, (2011), 511-521, Advances in Experimental Medicine and Biology, vol. 705, Springer, Boston, MA.
Van Der Holst, et al., "Proteins Involved in the Production and Perception of Oligosaccharides in Relation to Plant and Animal Development," (2001) Current Opinion in Structural Biology, 608-616, 11(5).

\* cited by examiner

SEQUENCE LISTING

<160> NUMBER OF SEQ ID NOS: 2

<210> SEQ ID NO 1
<211> LENGTH: 1458
<212> TYPE: DNA
<213> ORGANISM: Bacillus psychrosaccharolyticus

<400> SEQUENCE: 1

```
tgacgctggc ggcgtgccta atacatgcaa gtcgagcgga ttgttgagtt tactcaacaa    60
tcagcggcgg acgggtgagt aacacgtggg caacctgcct ataagactgg gataacttcg   120
ggaaaccgga gctaataccg gatatgttct tctctcgcat gagagaagat ggaaagacgg   180
tttcggctgt cacttataga tgggcccgcg gcgcattagc tagttggtga ggtaatggct   240
caccaaggca acgatgcgta gccgacctga gagggtgatc ggccacactg ggactgagac   300
acggcccaga ctcctacggg aggcagcagt agggaatctt ccgcaatgga cgaaagtctg   360
acggagcaac gccgcgtgaa acgatgaagg ctttcgggtc gtaaagttct gttgttaggg   420
aagaacaagt accagagtaa ctgctggtac cttgacggta cctaaccaga aagccacggc   480
taactacgtg ccagcagccg cggtaatacg taggtggcaa gcgttatccg gaattattgg   540
gcgtaaagcg cgcgcaggtg gttccttaag tctgatgtga agcccccgg ctcaaccggg    600 gagggtcatt ggaaactggg gaacttgagt gtagaagagg aaagtggaat tccacgtgta   660
gcggtgaaat gcgtagagat gtggaggaac accagtggcg aaggcgactt tctggtctat   720
aactgacact gaggcgcgaa agcgtgggga gcaaacagga ttagataccc tggtagtcca   780
cgccgtaaac gatgagtgct aagtgttaga gggtttccgc cctttagtgc tgcagctaac   840
gcattaagca ctccgcctgg ggagtacggc cgcaaggctg aaactcaaag gaattgacgg   900
gggcccgcac aagcggtgga gcatgtggtt taattcgaag caacgcgaag aaccttacca   960
ggtcttgaca tcctctgaca ctcctagaga taggacgttc cccttcgggg gacagagtga  1020
caggtggtgc atggttgtcg tcagctcgtg tcgtgagatg ttgggttaag tcccgcaacg  1080
agcgcaaccc ttgatcttag ttgccagcat tcagttgggc actctaaggt gactgccggt  1140
gataaaccgg aggaaggtgg ggatgacgtc aaatcatcat gccccttatg acctgggcta  1200
cacacgtgct acaatggatg gtacaaagag ctgcaaaccc gcgagggtaa gcgaatctca  1260
taaagccatt ctcagttcgg attgcaggct gcaactcgcc tgcatgaagc cggaatcgct  1320
agtaatcgcg gatcagcatg ccgcggtgaa tacgttcccg ggccttgtac acaccgcccg  1380
tcacaccacg agagtttgta acacccgaag tcggtgaggt aaccgcaagg agccagccgc  1440
ctaaggtggg acagatga                                                1458
```

<210> SEQ ID NO 2
<211> LENGTH: 1456
<212> TYPE: DNA
<213> ORGANISM: Bacillus psychrosaccharolyticus

<400> SEQUENCE: 2

```
atgacgctgg cggcgtgcct aatacatgca agtcgagcga attgttgagt ttactcaaca    60
```

-continued

```
gttagcggcg gacgggtgag taacacgtgg gcaacctgcc tataagactg ggataacttc    120
gggaaaccgg agctaatacc ggatatgttc ttttctcgca tgagaaaaga tggaaagacg    180
gtttcggctg tcacttatag atgggcccgc ggcgcattag ctagttggtg aggtaatggc    240
tcaccaaggc aacgatgcgt agccgacctg agagggtgat cggccacact gggactgaga    300
cacggcccag actcctacgg gaggcagcag tagggaatct tccgcaatgg acgaaagtct    360
gacggagcaa cgccgcgtga acgatgaagg ctttcgggtc gtaaagttct gttgttaggg    420
aagaacaagt accagagtaa ctgctggtac cttgacggta cctaaccaga aagccacggc    480
taactacgtg ccagcagccg cggtaatacg taggtggcaa gcgttatccg gaattattgg    540
gcgtaaagcg cgcgcaggtg gttccttaag tctgatgtga agcccccgg ctcaaccggg     600 gagggtcatt ggaaactggg gaacttgagt gtagaagagg aaagtggaat tccacgtgta    660
gcggtgaaat gcgtagagat gtggaggaac accagtggcg aaggcgactt tctggtctat    720
aactgacact gaggcgcgaa agcgtgggga gcaaacagga ttagataccc tggtagtcca    780
cgccgtaaac gatgagtgct aagtgttaga gggtttccgc cctttagtgc tgcagctaac    840
gcattaagca ctccgcctgg ggagtacggc cgcaaggctg aaactcaaag gaattgacgg    900
gggcccgcac aagcggtgga gcatgtggtt taattcgaag caacgcgaag aaccttacca    960
ggtcttgaca tcctctgaca ctcctagaga taggacgttc ccttcgggg acagagtga    1020 caggtggtgc atggttgtcg tcagctcgtg tcgtgagatg ttgggttaag tcccgcaacg   1080
agcgcaaccc ttgatcttag ttgccagcat tcagttgggc actctaaggt gactgccggt   1140
gataaaccgg aggaaggtgg ggatgacgtc aaatcatcat gccccttatg acctgggcta   1200
cacacgtgct acaatggatg gtacaaagag ctgcaaactc gcgagggtaa gcgaatctca   1260
taaagccatt ctcagttcgg attgcaggct gcaactcgcc tgcatgaagc cggaatcgct   1320
agtaatcgcg gatcagcatg ccgcggtgaa tacgttcccg ggccttgtac acaccgcccg   1380
tcacaccacg agagtttgta acacccgaag tcggtgaggt aaccgcaagg agccagccgc   1440
ctaaggtggg acagat                                                   1456
```

MICROBIAL COMPOSITIONS AND METHODS

REFERENCE TO RELATED APPLICATIONS

This application is a 371 National Stage application of International Application No. PCT/US2018/012084, filed Jan. 2, 2018, which claims the priority benefit of U.S. Provisional Application No. 62/441,929, filed Jan. 3, 2017, U.S. Provisional Application No. 62/449,981, filed Jan. 24, 2017, and U.S. Provisional Application No. 62/573,071, filed Oct. 16, 2017,the entire contents of each of which are herein incorporated by reference in their entirety.

INCORPORATION OF SEQUENCE LISTING

The sequence listing that is contained in the file named "MONS411WO_ST25.txt," which is 5 kilobytes as measured in Microsoft Windows operating system and was created on Jan. 2, 2018, is filed electronically herewith and incorporated herein by reference.

FIELD OF THE INVENTION

The present disclosure relates to compositions comprising microorganisms for increasing plant yield as well as methods for treating plants, plant parts, or soils to increase plant yield.

BACKGROUND

Some microorganisms, including bacteria and fungi, may positively affect plant health and growth under certain circumstances and improve yield of crop plants. Beneficial microbes may improve fertilization, nutrient availability or uptake, improve soil characteristics, modulate plant growth, or provide biopesticide or biocontrol activity. However, microbes may also negatively impact plants in some cases, and existing microbial products have sometimes exhibited inconsistent performance or minimal crop benefits.

A continuing need exists in the art for the development of novel microbial compositions and methods that can be used to improve yield of crop plants in a variety of agricultural field environments and growth conditions.

SUMMARY

In one aspect, an isolated *Bacillus psychrosaccharolyticus* strain is provided that is deposited as ATCC accession number PTA-123720 or PTA-124246. An isolated *Bacillus* strain may have a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, and wherein the *Bacillus* strain confers a positive agricultural trait or benefit to a crop plant when the crop plant is treated or associated with the *Bacillus* strain. An isolated *Bacillus* strain may have a whole (or partial) genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding genome sequence of a *Bacillus psychrosaccharolyticus* strain provided herein, and wherein the *Bacillus* strain confers a positive agricultural trait or benefit to a crop plant treated or associated with the *Bacillus* strain. A positive agricultural trait or benefit may be increased yield relative to a control plant. An isolated *Bacillus* strain may be a progeny of a *Bacillus psychrosaccharolyticus* strain provided herein. In further embodiments, a functional variant of a *Bacillus psychrosaccharolyticus* strain or isolate is provided. In further embodiments, a pure or substantially pure culture or population of a *Bacillus psychrosaccharolyticus* strain or a *Bacillus* strain or isolate is provided.

In another aspect, a composition is provided comprising a microbial strain or isolate and an agriculturally acceptable carrier, wherein the microbial strain or isolate has a 16S rDNA sequence that is at least 99.9% or at least 99.95% identical to SEQ ID NO: 1 and/or 2, or a microbial strain or isolate may have a 16S rDNA sequence that is 100% identical to SEQ ID NO: 1 and/or 2. Compositions may comprise a microbial strain or isolate having a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246.

In a further aspect, a composition is provided comprising a microbial strain or isolate and an agriculturally acceptable carrier, wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246. A microbial strain or isolate may be a *Bacillus psychrosaccharolyticus* strain or isolate. A bacterial strain or isolate may be deposited as ATCC accession number PTA-123720 or PTA-124246. In certain embodiments, an agriculturally acceptable carrier is provided that may confer at least one beneficial characteristic to the composition, such as improved efficacy, stability, wetting, flowability or coating onto a plant, plant part or seed, relative to a control composition lacking the agriculturally acceptable carrier. In further embodiments, compositions may comprise a wetting agent or dispersant, a binder or adherent, an aqueous solvent and a non-aqueous co-solvent. Compositions may further comprise a pesticidal agent; a fungicide, herbicide, insecticide, miticide, acaricide, nematicide, and/or gastropodicide; and/or a plant nutrient or fertilizer. Compositions provided herein may be formulated as a solid; as a powder, lyophilisate, pellet or granules; as a liquid or gel; or as an emulsion, colloid, suspension or solution.

Compositions may further comprise one or more of a lipo-chitooligosaccharide (LCO), a chitooligosaccharide (CO), a LCO-producing bacteria or fungus, and a chitinous compound; and/or one or more of a flavonoid, humic acid, fulvic acid, jasmonic acid or derivatives thereof, linoleic acid or derivatives thereof, linolenic acid or derivatives thereof, karrikin, and gluconolactone. In certain embodiments, compositions may comprise a microbial strain or isolate at a concentration of at least $10^3$ cfu per milliliter or gram. Compositions may comprise a pure or substantially pure population of the microbial strain or isolate. In certain embodiments, compositions are provided that confer a positive agricultural trait or benefit to a crop plant treated or associated with the composition, such as increased yield relative to a control plant.

In another aspect, a kit or container is provided comprising or containing a composition as described herein.

In further aspects, a plant, plant part or plant seed is provided that is associated with a composition described herein, such as a plant, plant part or plant seed having applied or coated on at least a portion of its outer surface a composition comprising a microbial strain or isolate, wherein the microbial strain or isolate is heterologous with respect to the plant, plant part or plant seed and has a 16S rDNA sequence that is at least 99.5%, at least 99.55%, at least 99.6%, at least 99.65%, at least 99.7%, at least 99.75%, at least 99.8%, at least 99.85%, at least 99.9% identical to SEQ ID NO: 1 and/or 2. In certain embodiments, a composition may be applied or coated on at least a portion of the outer surface of the plant, plant part or plant seed. In some embodiments, the plant, plant part or plant seed is transgenic. Also provided is a plant, plant part or plant seed having applied or coated on at least a portion of its outer surface a composition comprising a microbial strain or isolate, wherein the microbial strain or isolate is heterologous with respect to the plant, plant part or plant seed and has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246.

In certain embodiments, a composition may be applied or coated on at least a portion of the outer surface of the plant, plant part or plant seed. In some embodiments, the plant, plant part or plant seed is transgenic. Embodiments may comprise a plant seed having on at least a portion of its outer surface a composition comprising a microbial strain or isolate, wherein the microbial strain or isolate is heterologous with respect to the plant seed, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2. A plant seed may include, for example, a monocotyledonous plant seed, such as a plant seed from corn, wheat, rice, barley, oat, sorghum or other cereal plant.

According to another aspect, a bag or container is provided comprising or containing plant seeds or plant parts treated or coated with a composition disclosed herein.

In other aspects, plants are provided that are grown or developed from a plant seed or plant part coated, treated or associated with a microbial strain or isolate. In some embodiments, plants may exhibit increased yield relative to a control plant grown or developed from a plant seed or plant part that was not coated, treated or associated with the microbial strain or isolate.

In another aspect, methods are provided comprising: applying a composition to a plant, plant part or plant seed, the composition comprising a microbial strain or isolate and an agriculturally acceptable carrier, wherein the microbial strain or isolate is heterologous with respect to the plant, plant part or plant seed, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2. In some embodiments, the microbial strain or isolate has a 16S rDNA sequence that is 100% identical to SEQ ID NO: 1 or 2. In some embodiments, the microbial strain or isolate is the bacterial strain or isolate deposited as ATCC accession number PTA-123720 and/or PTA-124246. An applying step may comprise coating a composition onto at least a portion of the outer surface of the plant, plant part or plant seed.

In certain embodiments, methods may comprise applying a composition to a monocotyledonous plant seed, such as a corn, wheat, rice, barley, oat, sorghum or other cereal plant seed. In further embodiments, the applying step may comprise solid matrix priming, imbibing, coating, spraying, tumbling, agitating, dripping, soaking, immersing, dusting, drenching or encapsulating with the composition. In some embodiments, a composition may be applied to a crop plant, wherein the composition comprises an effective amount of a microbial strain or isolate to increase the yield of the crop plant. A composition may be applied to a plant part or plant seed, and the composition may comprise an effective amount of a microbial strain or isolate to increase the yield of a crop plant grown, developed or regenerated from the plant part or plant seed after planting.

In further aspects, methods for increasing the yield of a crop plant are provided comprising: (a) planting a plant part or seed, wherein the plant part or seed is at least partially coated with a composition comprising a microbial strain or isolate and an agriculturally acceptable carrier, wherein the microbial strain or isolate is heterologous with respect to the plant, plant part or plant seed, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, and (b) growing or regenerating the crop plant from the plant part or seed. Methods may further comprise the step of: (c) harvesting seed from the crop plant.

In yet another aspect, methods of increasing the yield of a crop plant are provided comprising: (a) applying to the crop plant a composition comprising a microbial strain or isolate and an agriculturally acceptable carrier, wherein the microbial strain or isolate is heterologous with respect to the crop plant, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, and (b) growing or developing the crop plant. In certain embodiments, methods may further comprise: (c) harvesting seed from the crop plant. In some embodiments, a composition may be applied as a foliar treatment. In some embodiments, crop plants produced by methods described herein may exhibit greater yield. In specific embodiments, the increased yield may result from increased biomass, increased grain weight per plot or per plant, greater resistance to lodging, increased root length, improved plant growth or vigor, increased stress tolerance, increased harvest index, increased fresh ear weight, increased ear diameter, increased ear length, increased seed size, increased seed number, or increased seed weight.

In some aspects, methods of increasing the yield of a crop plant are provided comprising: (a) applying to a growth medium associated with the crop plant a composition comprising a microbial strain or isolate and an agriculturally acceptable carrier, wherein the microbial strain or isolate is heterologous with respect to the crop plant, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, and (b) growing or developing the crop plant. In certain embodiments, methods may further comprise: (c) harvesting seed from the crop plant. Embodiments described herein may include methods wherein a composition is applied to a growth medium or soil, such as via a drip, spray, irrigation or soil drench.

In further aspects, methods of increasing the yield of a crop plant are provided comprising: (a) applying to a growth medium associated with a plant part or plant seed a composition comprising a microbial strain or isolate and an agriculturally acceptable carrier, wherein the microbial strain or isolate is heterologous with respect to the crop plant, and wherein the microbial strain or isolate has a partial or whole genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identical to the corresponding partial or whole genome sequence of the bacterial strain(s) or isolate(s) deposited as ATCC accession number PTA-123720 and/or PTA-124246, and/or a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, and (b) growing or regenerating the crop plant from the plant part or plant seed. In certain embodiments, methods may further comprise: (c) harvesting seed from the crop plant. In some embodiments, the composition may be applied to the growth medium as a drip, spray, irrigation or soil drench. In certain embodiments, the growth medium may be soil. Compositions may be applied to a growth medium before, simultaneously with, or after the plant part or plant seed being planted in the growth medium.

In another aspect, a modified microbial strain is provided having a 16S rDNA sequence that is at least 99.5%, at least 99.55%, at least 99.6%, at least 99.65%, at least 99.7%, at least 99.75%, at least 99.8%, at least 99.85%, at least 99.9%, at least 99.95%, or 100% identical to SEQ ID NO: 1 and/or 2, wherein the modified microbial strain confers a positive agricultural trait or benefit to a crop plant when the crop plant is treated or associated with the modified microbial strain. Further embodiments provide a modified microbial strain having a whole (or partial) genome sequence that is at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, or at least 99.95% identical to the corresponding partial or whole genome sequence of the bacterial strain(s) or isolate(s) deposited as ATCC accession number PTA-123720 and/or PTA-124246, wherein the modified microbial strain confers a positive agricultural trait or benefit to a crop plant when the crop plant is treated or associated with the modified microbial strain.

DETAILED DESCRIPTION

Multiple variables in a field or agricultural environment may affect the ability of microbes to provide a positive impact on yield. The present inventors have utilized agricultural field environments to test the ability of various microbial strains or isolates to improve yield of crop plants. By testing the ability of these microbial strains or isolates to positively impact plant yield under outdoor field conditions, numerous variables that could impact yield and affect the interaction between the microbe and the plant, such as weather conditions and humidity, day length, soil chemistry, and the surrounding atmosphere and microbiome in the soil, may be taken into account to measure yield. Thus, the present inventors have sought to identify microbial strains or isolates that positively impact yield of crop plants more directly under outdoor agricultural field conditions. Furthermore, by testing these microbes in a wide range of geographies, microbial strains or isolates may be identified that impact yield across a variety of different geographical field locations and growth conditions.

According to some embodiments, compositions are provided comprising a microbial strain or isolate discovered or identified under field conditions to impart or confer a positive agricultural trait or benefit to a crop plant, such as a monocot, cereal, corn or wheat plant, or a dicot plant, when associated with and/or applied to the crop plant. Such a positive agricultural trait or benefit may include increased yield of a crop plant. More specifically, the microbial strain or isolate may be a particular bacterial or *Bacillus* spp. or *Bacillus psychrosaccharolyticus* strain or isolate designated MON 202477 or MON 201251 and deposited under ATCC accession number PTA-123720 or PTA-124246, respectively, or a closely related *Bacillus* strain or isolate having the same or similar characteristic(s), such as the ability to confer or impart the same or similar positive agricultural trait or benefit to a crop plant. As described further below, the isolated MON 202477 strain has been shown in more than one year of testing to positively impact yield of corn plants across field testing geographies, and the MON 201251 strain has been shown to positively impact yield of corn and wheat plants across field testing geographies. Thus, compositions are provided comprising the isolated MON 202477 or MON 201251 strain for use in association with a crop plant, plant part or seed, as further provided herein.

Compositions of the present disclosure may comprise a *Bacillus* strain or isolate that is closely related to the isolated *Bacillus psychrosaccharolyticus* or *Bacillus* spp. strain(s) designated MON 202477 and/or MON 201251 and deposited under ATCC accession number PTA-123720 and PTA-124246, respectively, and having similar characteristic(s) in relation to a crop plant, such as the ability to impart the same or similar positive agricultural trait or benefit to the crop plant when applied to, or associated with, the crop plant. Without being bound by theory, a closely related *Bacillus* or *Bacillus psychrosaccharolyticus* strain or isolate having an identical or nearly identical genomic and/or 16S sequence as compared to the deposited MON 202477 and/or MON 201251 strain(s) may generally be expected to have similar characteristic(s) in relation to a crop plant, such as the ability to impart or confer the same or similar positive agricultural trait or benefit to the crop plant when applied to or associated with the crop plant. Indeed, a number of mutations in the genomic and/or 16S sequence of a *Bacillus* microbe relative to the MON 202477 and/or MON 201251 strain(s) may be inert with respect to its ability to impart or confer the same or similar positive agricultural trait or benefit to a crop plant.

Sequencing and comparison of the 16S rRNA-encoding DNA (16S rDNA) sequence is a method that has been used for determining the phylogeny or taxonomy of a microbial strain or isolate, which may also be used to define closely related microbial species, strains or isolates. Thus, the percent identity between the 16S rDNA sequences of two or more different microbial or bacterial strains or isolates may be used to indicate their relatedness to each other, with a higher percent identity indicating a closer relationship between the two or more microbial strains or isolates. A high degree of similarity or relatedness between two closely related microbial strains or isolates may also indicate a similar ability to impart the same or similar positive agricultural trait or benefit to a crop plant. Thus, according to some embodiments, compositions are provided comprising a *Bacillus* strain or isolate, such as a *Bacillus psychrosaccharolyticus* strain or isolate, that is closely related to the isolated MON 202477 and/or MON 201251 strain(s) and has a 16S rDNA sequence with a high percentage identity to the 16S rDNA sequence of the isolated MON 202477 and/or MON 201251 strain(s) (SEQ ID NO: 1 and/or 2), such as at least 99.5%, at least 99.6%, at least 99.7%, at least 99.8%, at least 99.9%, at least 99.95%, or 100% identity to the 16S rDNA sequence of the isolated MON 202477 and/or MON 201251 strain(s) (SEQ ID NO: 1 and/or 2), for use in association with a crop plant, plant part or seed, such as a monocot, cereal, corn or wheat plant, plant part or seed, as further provided herein. Given that two or more closely related microbial strains or isolates are more likely to impart or confer the same or similar positive agricultural trait or benefit to a crop plant when associated with or applied to the crop plant, a closely related *Bacillus* strain or isolate, such as a related *Bacillus psychrosaccharolyticus* strain or isolate, that imparts or confers the same or similar positive agricultural trait or benefit to a crop plant as the isolated MON 202477 and/or MON 201251 strain(s), may have a higher 16S rDNA sequence identity, such as at least 99.9%, at least 99.95%, or 100% identity, to the MON 202477 and/or MON 201251 strain(s).

Sequencing and comparison of aligned whole (or partial) genome sequences of microbial strains or isolates may be used to determine the phylogeny, taxonomy or classification of the microbial strain or isolate, which may be used to further define closely related microbial species, strains or isolates. Given the large sequence length for comparison, whole (or partial) genome sequences of two or more microbial strains or isolates may provide a greater degree of specificity and relatedness between the two or more microbial strains as opposed to other sequence comparisons. Accordingly, the aligned percent identity between the whole (or partial) genomic sequences of two or more different microbial or bacterial strains or isolates may be used to indicate their relatedness to each other, with a higher percent identity indicating a closer relationship between the two or more strains or isolates. Many mutations and differences in genomic sequence of a closely related *Bacillus* strain or isolate relative to the isolated MON 202477 and/or MON 201251 *Bacillus* strain(s) may be functionally inert, and thus may not change the characteristics or ability of the closely related *Bacillus* strain to impart or confer the positive agricultural trait or benefit to a crop plant. Thus, according to many embodiments, compositions are provided comprising a *Bacillus* strain or isolate, such as a *Bacillus psychrosaccharolyticus* strain or isolate, that is closely related to the isolated MON 202477 and/or MON 201251 strain(s) and has a whole (or partial) genome sequence with a high percentage identity to the corresponding whole (or partial) genome sequence of the isolated MON 202477 and/or MON 201251 strain(s) deposited under ATCC accession number PTA-123720 and PTA-124246, respectively, such as at least 99%, at least 99.1%, at least 99.2%, at least 99.3%, at least 99.4%, at least 99.5%, at least 99.55%, at least 99.6%, at least 99.65%, at least 99.7%, at least 99.75%, at least 99.8%, at least 99.85%, at least 99.9%, at least 99.95%, or 100% identity to the whole (or partial) genome sequence of the isolated MON 202477 and/or MON 201251 strain(s), which may be used in association with, and/or applied to, a crop plant, plant part or seed, such as a monocot, cereal, corn or wheat plant, plant part or seed, to impart or confer a positive trait or benefit to a crop plant. With regard to sequence comparisons between genomic or 16S rDNA sequences of two or more microbial strains, the term "corresponding" refers to the optimally aligned sequence. Thus, a genomic sequence of a first microbial strain would "correspond" to a genomic sequence of a second microbial strain if the genomic sequence of the first microbial strain is most optimally aligned with the genomic sequence of the second microbial strain relative to all other genomic sequences of the first microbial strain.

A microbial strain or isolate of the present disclosure may include a naturally occurring *Bacillus* strain or isolate, or a non-naturally occurring and/or mutant strain having one or more mutations, deletions, additions, insertions, rearrangements, etc., relative to the genomic and/or 16S rDNA sequence of the isolated MON 202477 and/or MON 201251 strain(s).

The terms "percent identity", "% identity" or "percent identical" as used herein in reference to two or more nucleotide or protein sequences is calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, as used herein, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

A microbial strain or isolate that is associated with, or applied to, a plant, plant part or plant seed as described herein, may be defined as being heterologous or heterologously applied in relation to the plant, plant part or plant seed. The terms "heterologous" or "heterologously applied" in relation to a plant, plant part or plant seed, or a growth medium or soil, refers to a microbial strain or isolate that is not detectably present on or in such plant, plant part or plant seed, or in such growth medium or soil, in nature and prior to the microbial strain or isolate being associated with, or applied to, the plant, plant part or plant seed or the growth medium or soil. Thus, according to some embodiments, compositions are provided comprising a microbial strain or isolate associated with a plant, plant part or plant seed, such as a monocot, cereal, corn or wheat plant, wherein the microbial strain or isolate is heterologous with respect to the plant, plant part or plant seed. According to some embodiments, compositions are provided comprising a microbial strain or isolate associated with a plant growth medium or soil, wherein the growth medium or soil is heterologous with respect to the microbial strain or isolate. Methods are provided wherein a microbial strain or isolate may be heterologously applied to a plant, plant part or plant seed, such as a monocot, cereal, corn or wheat plant. Methods are also provided wherein a microbial strain or isolate may be heterologously applied to a growth medium or soil. Such a microbial strain or isolate may be heterologously applied to a growth medium or soil at, near or surrounding a plant, plant part or plant seed, or at, near or surrounding where a plant part or plant seed will be planted in the growth medium or soil.

In addition to sequence identity or similarity, a closely related *Bacillus* microbial strain or isolate may be further defined as being able to impart or confer a positive trait or benefit to a crop plant, such as increased yield, growth and/or stress tolerance of the plant. A closely related *Bacillus* microbial strain or isolate may also have similar biochemical, molecular, secretory or metabolic characteristics or activities. For example, a related *Bacillus* microbial strain or isolate may have a positive activity for nitrate reduction according to standard assays.

Cultures of microorganisms may be prepared for use in microbial compositions using any standard or known static drying or liquid fermentation techniques known in the art. Optimal conditions for the cultivation of microorganisms may depend upon the particular strain. A person skilled in the art would be able to determine the appropriate nutrients and conditions. The microorganisms may be grown in aerobic liquid cultures on media which contain sources of carbon, nitrogen, and inorganic salts that can be assimilated by the microorganism and supportive of efficient cell growth. Carbon sources may include hexoses, such as glucose, and other sources that are readily assimilated such as amino acids, may be used. Many inorganic and proteinaceous materials may be used as nitrogen sources in the growth process. Nitrogen sources may include amino acids and urea, as well as ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the salts capable of yielding calcium, zinc, iron, manganese, magnesium, copper, cobalt, potassium, sodium, molybdate, phosphate, sulfate, chloride, borate, and like ions.

According to embodiments of the present disclosure, compositions are provided comprising various formulations of a microbial or bacterial strain or isolate as provided herein. Such formulations may include various salts, fillers, binders, solvents, carriers, excipients, adjuvants, and/or other components or ingredients, such as further described below. The amount and concentration of each component in a composition of the present disclosure may depend on many factors, such as the type, size and volume of material to which the composition will be applied, the type(s) of microorganisms in the composition, the number of microorganisms in the composition, the stability of the microorganisms in the composition, storage conditions (e.g., temperature, relative humidity, duration), etc. One skilled in the art would understand how to determine acceptable, effective and appropriate amounts and concentrations for various formulation components of microbial compositions of the present disclosure. In some embodiments, compositions of the present disclosure may comprise one or more carriers in an amount/concentration of about 1 to about 99% or more (by weight or volume based on the total weight or volume of the composition). For example, compositions of the present disclosure may comprise one or more carriers and/or other components in an amount or concentration of about 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99 or 99.5% or more (by weight or volume). The microbial strain or isolate may be present in a composition or formulation in any suitable form(s). According to some embodiments, the microbial strain or isolate may be a bacterial endophyte or a root or phylloplane colonizer. According to some embodiments, the microbial strain or isolate may be in the form of vegetative cells and/or spores.

Compositions and formulations may comprise a pure or substantially pure population or culture of a microbial strain or isolate described herein. A pure population or culture of a microbial strain or isolate refers to a population or culture of that strain or isolate that is free or essentially free of contamination of other microorganisms, such that the population or culture has sufficient genetic uniformity in terms of sequence identity, and different subcultures taken therefrom will exhibit substantially identical phenotypes and/or effects on agricultural crop plants. According to some embodiments, a microbial strain or isolate may be "purified," and the purified microbial strain or isolate may be combined with one or more other ingredients to form a composition or formulation. Any suitable method known in the art may be used to isolate and/or purify a particular microbial strain or isolate to form a pure or substantially pure population or culture of the microbial strain or isolate, such as by colony or clonal selection. Alternatively, the microbial strain or isolate may be mixed with other microorganisms to varying extents or proportions. According to some embodiments, the microbial strain or isolate may be present in a composition or formulation in an amount or concentration that is between 10-30%, 10-40%, 10-50%, 20-40%, 30-50%, greater than 50%, greater than 60%, greater than 70%, greater than 80%, greater than 90%, greater than 95%, greater than 96%, greater than 97%, greater than 98%, greater than 99%, or greater than 99.5% of the total population of microorganisms present in the composition or formulation. A composition comprises a "substantially pure" population or culture of a microbial strain or isolate if the strain or isolate accounts for greater than 95% of the total population of microorganisms present in the composition, such that at least 95%, at least 96%, at least 97%, at least 98%, at least 99%, at least 99.5%, at least 99.9%, or at least 99.95% of the subcultures taken therefrom exhibit identical genotypes and phenotypes. A composition comprises a "pure" population or culture of a microbial strain or isolate if the strain or isolate accounts for 100% of the total population of microorganisms present in the composition, such that 100% of the subcultures taken therefrom exhibit identical genotypes and phenotypes.

According to some embodiments, compositions and formulations may comprise an "effective amount", "effective concentration", and/or "effective dosage" of a microbial strain or isolate to impart a positive trait or benefit to a crop plant, such as increased yield, stress tolerance, nutrient availability or uptake, or improved soil characteristics, when used in association with the crop plant. The effective amount/concentration/dosage of the microbial strain or isolate may depend on a number of factors, such as the type, size and volume of seeds or plant material to which the composition or formulation will be applied, the magnitude of the desired benefit, trait or effect, the stability of the microbe in the composition or formulation or when applied to a plant, plant part or plant seed, the identity and amounts of other ingredients in the composition or formulation, the manner of application to a seed, plant material, soil or growth medium, and the relevant storage conditions (e.g., temperature, relative humidity, duration of storage, lighting, etc.). Those skilled in the art may determine an effective amount/concentration/dosage using dose-response experiments or other known method.

According to some embodiments, a microbial strain or isolate may be present in a composition at an amount or concentration ranging from about $1\times10^1$ to about $1\times10^{15}$ colony forming units (cfu) per gram or milliliter. For example, a microbial strain or isolate may be present in a composition at an amount or concentration of at least $1\times10^1$, at least $1\times10^2$, at least $1\times10^3$, at least $1\times10^4$, at least $1\times10^5$, at least $1\times10^6$, at least $1\times10^7$, at least $1\times10^8$, at least $1\times10^9$, at least $1\times10^{10}$, at least $1\times10^{11}$, at least $1\times10^{12}$, at least $1\times10^{13}$, at least $1\times10^{14}$, or at least $1\times10^{15}$ (or more) cfu per gram or milliliter of the composition. As used herein, the term "colony forming unit" or "cfu" refers to a microbial cell or spore capable of propagating on or in a suitable growth medium or substrate (e.g., a soil) when conditions (e.g., temperature, moisture, nutrient availability, pH, etc.) are favorable for germination and/or microbial growth.

According to further embodiments, a microbial strain or isolate may be present in a composition in an amount or concentration that is within a range from about 0.1% to 100% (by weight) of the composition, or from about 0.1% to about 90%, or from about 1% to about 90%, or from about 0.1% to about 80%, or from about 0.1% to about 70%, or from about 0.1% to about 60%, or from about 0.1% to about 50%, or from about 0.1% to about 40%, or from about 0.1% to about 30%, or from about 0.1% to about 20% (by weight) of the composition. For example, the microbial strain or isolate of the present disclosure may be present in an amount or concentration that is about 0.1%, 0.2%, 0.3%, 0.4%, 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, 96%, 97%, 98%, or 99% or more (by weight) of the composition. According to some embodiments, the amount/concentration of the microbial strain or isolate is about 1% to about 25%, about 5% to about 20%, about 5% to about 15%, about 5% to about 10%, or about 8% to about 12% (by weight) of the composition.

Compositions may comprise an isolated microbial strain described herein. A microbial strain has been "isolated" if it has been removed and/or purified from its natural environment. Such an "isolated" microbial strain may be the isolated MON 202477 or MON 201251 strain, a representative sample of which is deposited under ATCC accession number PTA-123720 and PTA-124246, respectively, or any functional variant thereof. Similarly, an "isolate" is a particular microbial strain that has been removed and/or purified from the environment. A "functional variant" of a microbial strain or isolate, such as the MON 202477 or MON 201251 isolate, may be defined as a strain or progeny thereof having high sequence identity (e.g., at least 99.5% identity (or greater) to the 16S rDNA sequence and/or at least 99% identity (or greater) to the whole (or partial) genomic sequence of the microbial strain or isolate, such as the MON 202477 and/or MON 201251 strain(s), as described above) and having or exhibiting the same or similar functional characteristics as the microbial strain or isolate, such as the isolated MON 202477 and/or MON 201251 strain(s). For example, similar to the isolated MON 202477 and/or MON 201251 strains, a functional variant may impart or confer a positive trait or benefit to a crop plant, such as increased yield, growth and/or stress tolerance of the plant, increased nutrient uptake by the plant itself or via increased nutrient availability and/or improved soil characteristics, and/or provide or have activity for nitrate reduction. Such a functional variant may exhibit the same or similar functional characteristic to the same extent, or to a greater or lesser extent or degree than the MON 202477 and/or MON 201251 strain(s), such as at least 70%, at least 75%, at least 80%, at least 85%, at least 90%, at least 95%, at least 96%, at least 97%, at least 98%, at least 99%, or 100% of the extent or degree of the functional characteristic, relative to the isolated MON 202477 and/or MON 201251 strain(s).

Compositions in some embodiments may comprise a modified microbial strain. As used herein, the term "modified microbial strain" refers to a microbial strain that is modified from a strain or isolate provided herein. Modified microbial strains may be produced by any suitable method(s), including, but not limited to, an induced mutation, including but not limited to a chemically induced mutation, to a polynucleotide within any genome of the strain or isolate; an insertion or deletion of one or more nucleotides within any genome within the strain or isolate, or combinations thereof; an inversion of at least one segment of DNA within any genome within the strain or isolate; a rearrangement of any genome within the strain or isolate; a generalized or specific transduction of homozygous or heterozygous polynucleotide segments into any genome within the strain or isolate; an introduction of one or more phage into any genome of the strain or isolate; a transformation of any strain or isolate resulting in the introduction into the strain or isolate of stably and autonomously replicating extrachromosomal DNA; any change to any genome or to the total DNA composition within the strain or isolate as a result of conjugation with any different microbial strain; and any combination of the foregoing. The term "modified microbial strain" includes a strain or isolate with (a) one or more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by, for example, deleting nucleotide sequence, and (d) added extrachromosomal DNA. In some embodiments, a "modified microbial strain" comprises a combination of two or more nucleotide sequences (e.g., two or more naturally occurring genes that do not naturally occur in the same microbial strain or isolate) or comprise a nucleotide sequence isolated from nature at a locus that is different from the natural locus.

Compositions of the present disclosure may further comprise an agriculturally acceptable carrier in combination with the microbial strain or isolate. As used herein, the term "agriculturally acceptable" in reference to a carrier, material, ingredient, or substance of a microbial composition comprising a microbial strain or isolate means that the carrier, material, ingredient or substance, as the case may be, (i) is compatible with other ingredients of the microbial composition at least for the purpose in which the microbial composition will be used, (ii) can be included in the microbial composition to effectively and viably deliver the microbial strain or isolate to a plant, plant part, plant seed, or plant growth medium (e.g., soil), (iii) is not normally associated with the microbial strain or isolate in nature (at least in the form in which it will be used), and (iv) is not deleterious to a plant, plant part, or plant seed to which the composition will be associated or applied (at least in the manner and amount in which it will be applied to, or associated with, the plant, plant part, or plant seed).

A "carrier" is defined as any substance or material that may be used and/or combined with a microbial strain or isolate to improve the delivery or effectiveness of the microbial strain or isolate to a plant, plant part or plant seed. An agriculturally acceptable carrier may include a soil-compatible carrier, a seed-compatible carrier, and/or a foliar-compatible carrier. As used herein, the term "soil-compatible carrier" refers to a material that can be added or applied to a soil without causing/having an unduly adverse effect on plant yield, soil structure, soil drainage, or the like. The term "seed-compatible carrier" refers to a material that can be added or applied to a seed without causing/having an unduly adverse effect on the seed, seed germination, the plant that grows from the seed, or the like. The term "foliar-compatible carrier" refers to a material that can be added or applied to an above ground portion of a plant or plant part without causing/having an unduly adverse effect on plant yield, plant health, or the like. Selection of appropriate carrier materials will depend on the intended application(s) and the microorganism(s) present in the composition. The carrier material(s) may be selected and/or combined to provide a composition or formulation in the form of a liquid, gel, slurry, or solid. Compositions may comprise one or more liquid and/or gel carriers, and/or one or more aqueous and/or non-aqueous solvents. As used herein, the term "non-aqueous" may refer to a composition, solvent or substance that comprises no more than a trace amount of water (e.g., no more than 0.5% water by weight).

According to some embodiments, compositions may be in solid or powder form and/or comprise one or more solid carriers. For example, compositions may comprise one or more powders (e.g., wettable powders) and/or granules. Non-limiting examples of solid carriers that can be useful in compositions of the present disclosure include peat-based powders and granules, freeze-dried powders, spray-dried powders, and combinations thereof.

Additional examples of carriers that can be included in compositions of the present disclosure can be found in Burges, H. D., Formulation of Microbial Biopesticides: Beneficial Microorganisms, Nematodes and Seed Treatments, Springer Science & Business Media (2012); and Inoue & Horikoshi, J. FERMENTATION BIOENG.71(3): 194 (1991), the contents and disclosures of which are incorporated herein by reference.

Compositions in some embodiments may be in liquid or gel form and/or comprise one or more liquid and/or gel carriers. Carriers in compositions or formulations may comprise a growth medium or broth suitable for culturing one or more of the microorganisms in the composition. For example, compositions may comprise a Czapek-Dox medium, a glycerol yeast extract, a mannitol yeast extract, a potato dextrose broth, and/or a YEM media. Commercial carriers may be used in accordance with a manufacturer's recommended amounts or concentrations.

Compositions may comprise one or more various solvents, such as organic, inorganic, non-aqueous and/or aqueous solvent(s). Examples of inorganic solvents include decane, dodecane, hexylether, and nonane. Examples of commercially available organic solvents include pentadecane, ISOPAR M, ISOPAR V, and ISOPAR L (Exxon Mobil). Additional examples of solvents that may be included in compositions and formulations can be found in Burges, supra; Inoue & Horikoshi, supra, the contents and disclosures of which are incorporated herein by reference. According to some embodiments, an aqueous solvent, such as water, may be combined with a co-solvent, such as ethyl lactate, methyl soyate/ethyl lactate co-solvent blends (e.g., STEPOSOL, available from Stepan), isopropanol, acetone, 1,2-propanediol, n-alkylpyrrolidones (e.g., the AGSOLEX series, available from ISP), a petroleum based-oil (e.g., AROMATIC series and SOLVESSO series available from Exxon Mobil), isoparaffinic fluids (e.g., ISOPAR series, available from Exxon Mobil), cycloparaffinic fluids (e.g., NAPPAR 6, available from Exxon Mobil), mineral spirits (e.g., VARSOL series available from Exxon Mobil), and mineral oils (e.g., paraffin oil). According to some embodiments, compositions may comprise one or more co-solvent(s) in addition to an aqueous solvent or water. Such co-solvent(s) may include, for example, non-aqueous solvents, such as one or more the foregoing non-aqueous solvents.

According to some embodiments, compositions including formulations may have a desired pH in a range from about 4.5 to about 9.5. Compositions of the present disclosure may comprise any suitable pH buffer(s) known in the art. For example, compositions may have a pH in a range from about 6 to about 8, or a pH of about 5, 5.5, 6, 6.5, 7, 7.5, 8 or 8.5. To maintain a desired pH, a composition may comprise one or more bufferes in a buffer solution. pH buffers may be selected to provide an aqueous composition having a pH of less than 10, typically from about 4.5 to about 9.5, from about 6 to about 8, or about 7. Buffer solutions suitable for a variety of pH ranges are known in the art.

Compositions may comprise one or more thickeners, rheology modifying agents, or stabilizing agents ("stabilizers"). Examples of stabilizers include anionic polysaccharides and cellulose derivatives. A stabilizer may comprise, for example, a clay, a silica, or a colloidal hydrophilic silica. Non-limiting examples of commercially available stabilizers include KELZAN CC (Kelco), methyl cellulose, carboxymethylcellulose and 2-hydroxyethylcellulose, hydroxymethylcellulose, kaolin, maltodextrin, malt extract, microcrystalline cellulose, and hygroscopic polymers. A non-limiting example of a commercially available colloidal hydrophilic silica is AEROSIL (Evonik). A stabilizer may also include a monosaccharide, disaccharide or sugar alcohol, such as maltose, trehalose, lactose, sucrose, cellobiose, mannitol, xylitol, or sorbitol, and any combination thereof. A stabilizer component may comprise from about 0.05% to about 10% by weight of a composition. For example, a stabilizer component may comprise from about 0.1% to about 5%, from about 0.1% to about 2%, or from about 0.1% to about 1% by weight of a composition.

Compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders, which are soluble or dispersible in water, co-polymers of two or more monomers, such as acrylic acid, methacrylic acid, itaconic acid, maleic acid, fumaric acid, maleic anhydride, vinylpyrrolidone, ethylenically unsaturated monomers, such as ethylene, butadiene, isoprene, chloroprene, styrene, divinylbenzene, ot-methylstyrene or p-methylstyrene, vinyl halides, such as vinyl chloride and vinylidene chloride, vinyl esters, such as vinyl acetate, vinyl propionate or vinyl stearate, vinyl methyl ketones or esters of acrylic acid or methacrylic acid with monohydric alcohols or polyols, such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, diethyl esters or monoesters of unsaturated dicarboxylic acids, (meth)acrylamido-N-methylol methyl ether, amides or nitriles, such as acrylamide, methacrylamide, N-methylol(meth)acrylamide, acrylonitrile, methacrylonitrile, N-substituted maleiraides, and ethers, such as vinyl butyl ether, vinyl isobutyl ether or vinyl phenyl ether, and combinations thereof.

Compositions in some embodiments may comprise one or more oxidation control components, which may include one or more antioxidants (e.g., one or more of: ascorbic acid, ascorbyl palmitate, ascorbyl stearate, calcium ascorbate, carotenoids, lipoic acid, phenolic compounds (e.g., one or more flavonoids, flavones and/or flavonols), potassium ascorbate, sodium ascorbate, one or more thiols (e.g., glutathione, lipoic acid and/or N-acetyl cysteine), tocopherols, one or more tocotrienols, ubiquinone and/or uric acid) and/or one or more oxygen scavengers, such as ascorbic acid and/or sodium hydrogen carbonate.

Composition in some embodiments may comprise one or more UV protectants, such as one or more aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates). Non-limiting examples of UV protectants include Borregaard LignoTech™ lignosulfonates (e.g., Borresperse 3A, Borresperse CA, Borresperse NA, Marasperse AG, Norlig A, Norlig 11D, Ufoxane 3A, Ultrazine NA, Vanisperse CB; Borregaard Lignotech, Sarpsborg, Norway) and combinations thereof. See, for example, BURGES, FORMULATION OF MICROBIAL BIOPESTICIDES: BENEFICIAL MICROORGANISMS, NEMATODES AND SEED TREATMENTS (Springer Science & Business Media) (2012).

Compositions in some embodiments may comprise one or more agriculturally acceptable polymers, such as agar, alginate, carrageenan, cellulose, guar gum, locust bean gum, methylcellulose, pectin, polycaprolactone, polylactide, polyvinyl alcohol, polyvinyl pyrrolidone, sodium carboxymethyl cellulose, starch and/or xanthan gum. In an aspect, the one or more polymers is a natural polymer (e.g., agar, starch, alginate, pectin, cellulose, etc.), a synthetic polymer, a biodegradable polymer (e.g., polycaprolactone, polylactide, polyvinyl alcohol, etc.), or a combination thereof. For a non-limiting list of polymers useful for the compositions described herein, see, e.g., Pouci et al., *Am. J. Agri. & Biol. Sci.*, 3(1):299-314 (2008), the content and disclosure of which are incorporated herein by reference.

Compositions in some embodiments may comprise one or more agriculturally acceptable dispersants, which may include one or more surfactants and/or wetting agents. Dispersants may be used to maintain a homogeneous or even distribution of particles or cells in a suspension, such as an even or homogeneous distribution of a microbial strain or isolate, which may be particularly useful for solid or dried formulations of a microbe and/or liquid formulations or fermentates. In addition to maintaining an even distribution of the microbe in a final composition or formulation and during application of a composition or formulation to a plant, plant part or plant seed, a dispersant or wetting agent may also facilitate mixing of a microbe with other ingredients and solvents of a microbial formulation or composition and avoid aggregation or clumping of particles, or their adherence to container walls, etc., during formulation of a microbial composition. A dispersant may reduce the cohesiveness of like particles, the surface tension of a liquid, the interfacial tension between two liquids, and/or the interfacial tension between or a liquid and a solid. Compositions may comprise a primary dispersant in combination with one or more secondary dispersants, and the primary and secondary dispersants may be different types (e.g., non-ionic, cationic, anionic, and/or zwitterionic). Wetting agents may be used with compositions applied to soils, particularly hydrophobic soils, to improve the infiltration and/or penetration of water into a soil. The wetting agent or dispersant may be an adjuvant, oil, surfactant, buffer, acidifier, or combination thereof. The wetting agent or dispersant may be a surfactant, such as one or more non-ionic surfactants, one or more cationic surfactants, one or more anionic surfactants, one or more zwitterionic surfactants, or any combination thereof.

Selection of an appropriate dispersant(s) will depend on the intended application(s) and the microorganism(s) present in the composition, but will typically have little or no toxicity for the microorganism(s) in the inoculant composition and for the plant part(s) to which the composition is to be applied. In some embodiments, the dispersant(s) will be selected to wet and/or emulsify one or more soils. Non-limiting examples of dispersants include Atlox™ (e.g., 4916, 4991; Croda International PLC, Edison, N.J.), Atlox METASPERSE™ (Croda International PLC, Edison, N.J.), BIO-SOFT® (e.g., N series, such as N1-3, N1-7, N1-5, N1-9, N23-3, N2.3-6.5, N25-3, N25-7, N25-9, N91-2.5, N91-6, N91-8; Stepan Company, Northfield, Ill.), MAKON® nonionic surfactants (e.g., DA-4, DA-6 and DA-9; Stepan Company, Northfield, Ill.), MORWET® powders (Akzo Nobel Surface Chemistry LLC, Chicago, Ill.), MULTIWET™ surfactants (e.g., MO-85P-PW-(AP); Croda International PLC, Edison, N.J.), SILWET® L-77 (Helena Chemical Company, Collierville, Tenn.), SPAN™ surfactants (e.g., 20, 40, 60, 65, 80 and 85; Croda Inc., Edison N.J.), TAMOL™ dispersants (The Dow Chemical Company, Midland, Mich.), TERGITOL™ surfactants (e.g., TMN-6 and TMN-100X; The Dow Chemical Company, Midland, Mich.), TERSPERSE surfactants (e.g., 2001, 2020, 2100, 2105, 2158, 2700, 4894 and 4896; Hunstman Corp., The Woodlands, Tex.), TRITON™ surfactants (e.g., X-100; The Dow Chemical Company, Midland, Mich.), TWEEN® surfactants (e.g., TWEEN® 20, 21, 22, 23, 28, 40, 60, 61, 65, 80, 81 and 85; Croda International PLC, Edison, N.J.), and combinations thereof. Non-limiting examples of wetting agents include naphthalene sulfonates, alkyl naphthalene sulfonates (e.g., sodium alkyl naphthalene sulfonate), isopropyl naphthalene sulfonates (e.g., sodium isopropyl naphthalene sulfonate) and/or butyl naphthalene sulfonates (e.g., sodium n-butyl naphthalene sulfonate). Additional examples of dispersants may be found in BAIRD & ZUBLENA. 1993. SOIL FACTS: USING WETTING AGENTS (NON-IONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); and MCCARTY, WETTING AGENTS (Clemson University Cooperative Extension Service Publication) (2001).

Non-liming examples of anionic surfactants include one or more alkyl carboxylates (e.g., sodium stearate), alcohol ether carboxylates, phenol ether carboxylates, alkyl sulfates (e.g., alkyl lauryl sulfate and/or sodium lauryl sulfate), alkyl ether sulfates, alcohol sulfates, alcohol ether sulfates, alkyl amido ether sulfates, alkyl aryl ether sulfates, alkyl aryl polyether sulfates, alkyl aryl sulfates, alkyl aryl sulfonates, alkyl sulfonates, alkyl amide sulfonates, aryl sulfonates, alkyl benzene sulfonates, alkyl diphenyloxide sulfonate, alpha-olefin sulfonates, alkyl naphthalene sulfonates, paraffin sulfonates, sulfosuccinates, alkyl sulfosuccinates, alkyl ether sulfosuccinates, alkylamide sulfosuccinates, mono- or disulfosuccinate esters of alcohols or polyalkoxylated alkanols, alkyl sulfosuccinamate, alkyl sulfoacetates, alkyl phosphates, alkyl ether phosphates, mono- or diphosphate esters of polyalkoxylated alkyl alcohols or alkyl phenols, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, toluene sulfonates and/or xylene sulfonates), ionic surfactants (e.g., one or more ethers, glycol ethers, ethanolamides, sulfoanylamides, alcohols, amides, alcohol ethoxylates, glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, polyoxyethylenated polyoxyproylene glycols, sorbitan fatty esters, sorbitan fatty acid alcohol ethoxylates and/orsorbitan fatty acid ester ethoxylates), nonionic surfactants (e.g., one or more alcohol ethoxylates, alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers (e.g.,), glycerol esters, glycol alkyl ethers (e.g., polyoxyethylene glycol alkyl ethers, polyoxypropylene glycol alkyl ethers,), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers (e.g., Triton X-100), polyvinyl pynolidones, sugar-based alkyl polyglycosides, sulfoanylamides, sorbitan fatty acid alcohol ethoxylates, sorbitan fatty acid ester ethoxylates, sorbitan fatty acid esters, tertiary acetylenic glycols and/or TWEEN 80), styrene acrylic polymers, modified styrene acrylic polymers and/or zwitterionic surfactants (e.g., 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins. Anionic surfactants may be either water soluble anionic surfactants, water insoluble anionic surfactants, or a combination of water soluble anionic surfactants and water insoluble anionic surfactants.

Other non-limiting examples of commercially available anionic surfactants include sodium dodecylsulfate (Na-DS, SDS), MORWET D-425 (a sodium salt of alkyl naphthalene sulfonate condensate, available from Akzo Nobel), MORWET D-500 (a sodium salt of alkyl naphthalene sulfonate condensate with a block copolymer, available from Akzo Nobel), sodium dodecylbenzene sulfonic acid (Na-DBSA) (Aldrich), diphenyloxide disulfonate, naphthalene formaldehyde condensate, DOWFAX (Dow), dihexylsulfosuccinate, and dioctylsulfosuccinate, TWEEN®, alkyl naphthalene sulfonate condensates, and salts thereof.

Non-limiting examples of non-ionic surfactants include sorbitan esters, ethoxylated sorbitan esters, alkoxylated alkylphenols, alkoxylated alcohols, block copolymer ethers, and lanolin derivatives. In accordance with an aspect, the surfactant comprises an alkylether block copolymer. Other non-limiting examples of water insoluble nonionic surfactants include alkyl and aryl: glycerol ethers, glycol ethers, ethanolamides, sulfoanylamides, alcohols, amides, alcohol ethoxylates (e.g., TERGITOL™ 15-S surfactants, such as TERGITOL™15-S-9 (The Dow Chemical Company, Midland, Mich.)), glycerol esters, glycol esters, ethoxylates of glycerol ester and glycol esters, sugar-based alkyl polyglycosides, polyoxyethylenated fatty acids, alkanolamine condensates, alkanolamides, tertiary acetylenic glycols, polyoxyethylenated mercaptans, carboxylic acid esters, cetostearyl alcohol, cetyl alcohol, cocamide DEA, dodecyldimethylamine oxides, ethanolamides, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers or polyoxypropylene glycol alkyl ethers), glycol alkylphenol ethers (e.g., polyoxyethylene glycol alkylphenol ethers), monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pynolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols, polyoxyethylenated polyoxyproylene glycols, sorbitan fatty esters, or combinations thereof. Also included are EO/PO block copolymers (EO is ethylene oxide, PO is propylene oxide), EO polymers and copolymers, polyamines, and polyvinylpynolidones.

Further non-limiting examples of water soluble non-ionic surfactants include sorbitan fatty acid alcohol ethoxylates and sorbitan fatty acid ester ethoxylates. Further non-limiting examples of commercially available non-ionic surfactants include SPAN 20, SPAN 40, SPAN 80, SPAN 65, and SPAN 85 (Aldrich); TWEEN 20, TWEEN 40, TWEEN 60, TWEEN 80, and TWEEN 85 (Aldrich); IGEPAL CA-210, IGEPAL CA-520, IGEPAL CA-720, IGEPAL CO-210, IGEPAL CO-520, IGEPAL CO-630, IGEPAL CO-720, IGEPAL CO-890, and IGEPAL DM-970 (available from Aldrich); Triton X-100 (Aldrich); BRIJ S10, BRIJ S20, BRIJ 30, BRIJ 52, BRIJ 56, BRIJ 58, BRIJ 72, BRIJ 76, BRIJ 78, BRIJ 92V, BRIJ 97, and BRIJ 98 (Aldrich); PLURONIC L-31, PLURONIC L-35, PLURONIC L-61, PLURONIC L-81, PLURONIC L-64, PLURONIC L-121, PLURONIC 10R5, PLURONIC 17R4, and PLURONIC 31R1 (Aldrich); Atlas G-5000 and Atlas G-5002L (Croda); ATLOX 4912 and ATLOX 4912-SF (Croda); and SOLUPLUS (BASF), LANEXOL AWS (Croda). Compositions may comprise at least one or more nonionic surfactants, such as at least one water-insoluble nonionic surfactant, at least one water soluble nonionic surfactant, or combinations thereof. In still another aspect, the compositions comprise a combination of nonionic surfactants having hydrocarbon chains of substantially the same length.

Non-limiting examples of cationic surfactants include mono alkyl quaternary amine, fatty acid amide surfactants, amidoamine, imidazoline, and polymeric cationic surfactants. According to some embodiments, the composition comprises one or more pH-dependent amines, quaternary ammonium cations, alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide, and/or octenidine dihydrochloride, and combinations thereof.

Non-limiting examples of zwitterionic surfactants include one or more betaines and/or one or more sultaines, 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine, and sphingomyelins, and combinations thereof.

Surfactants may also include soaps, organosilicone surfactants, and silicone-based antifoams used as surfactants in silicone-based and mineral-oil based antifoams. In yet another aspect, compositions may also comprise alkali metal salts of fatty acids (e.g., water soluble alkali metal salts of fatty acids and/or water insoluble alkali metal salts of fatty acids).

Compositions in some embodiments may comprise at least 5 g/L, at least 10 g/L, at least 15 g/L, at least 20 g/L, at least 25 g/L, at least 30 g/L, at least 35 g/L, at least 40 g/L, at least 45 g/L, or at least 50 g/L of a dispersant(s). In some embodiments, the dispersant may be from about 1 to about 100 g/L, from about 5 to about 75 g/L, or from about 20 to about 50 g/L. The amount of dispersants may also be expressed as a percentage by weight of a composition, such as about 0.5% to about 20%, from about 0.5% to about 10%, from about 0.5% to about 5%, from about 0.5% to about 8%, from about 0.5% to about 5%, or from about 1% to about 4% by weight of the composition.

Compositions in some embodiments may comprise one or more agriculturally acceptable drying agents or drying powders, such as calcium stearate, one or more clays, graphite, magnesium stearate, magnesium sulfate, powdered milk, one or more silica powders, soy lecithin and/or talc. Other non-limiting examples of drying agents include AEROSIL® hydrophobic fumed silica powders (Evonik Corporation, Parsippany, N.J.), BENTOLITE® powders (BYK-Chemie GmbH, Wesel, Germany), INCOTEC® powders (INCOTEC Inc., Salinas, Calif.), SIPERNAT® silica powders (Evonik Corporation, Parsippany, N.J.) and combinations thereof. Additional examples of drying agents may be found in BURGES, FORMULATION OF MICROBIAL BIOPESTICIDES: BENEFICIAL MICROORGANISMS, NEMATODES AND SEED TREATMENTS (Springer Science & Business Media) (2012).

Compositions in some embodiments may comprise one or more anti-freezing agents. For example, an anti-freezing agent may include one or more of ethylene glycol, alcohol, butanediol, pentanediol, mannitol, sorbitol, glycerol (glycerine), propylene glycol and/or urea. The antifreeze agent may be present in a composition at a concentration of at least 5 g/L, at least 10 g/L, at least 15 g/L, at least 20 g/L, at least 30 g/L, at least 40 g/L, at least 50 g/L, at least 60 g/L, at least 70 g/L, or at least 80 g/L, such as from about 1 to about 150 g/L, from about 10 to about 100 g/L, or from about 20 to about 80 g/L.

Compositions in some embodiments may comprise one or more functionalized dendrimers to enhance the efficacy and/or stability of the composition. Non-limiting examples of classes of functionalized dendrimers include poly(amidoamine) (PAMAM, Generations 0-7), poly(amidoamine-organosilicone) (PAMAMOS), polypropylene imidine) (PPI, Generations 0-5), poly(benzylethers) (Frechet-type), Arobols (Newkome type), poly(phenylacetylenes) and surface engineered dendrimers (e.g. PEGylated dendrimers, glycodendrimers, peptide funtionalized dendrimers, and galabiose-functionalized dendrimers). Dendrimer(s) may comprise at least 0.1% and up to 10% or more, or from about 1% to about 10%, of the composition by weight.

Compositions in some embodiments may comprise one or more antifoam agents. Examples of antifoam agents include organosilicone or silicone-free compounds. Non-limiting examples of commercially available antifoam products include Break-Thru OE441 (Evonik), Break-Thru AF9905 (Evonik), AGNIQUE DF 6889 (Cognis), AGNIQUE DFM 111S (Cognis), BYK-016 (BYK), FG-10 antifoam emulsion (Dow Corning), 1520-US (Dow Corning), 1510-US (Dow Corning), SAG 1538 (Momentive), and SAG 1572 (Momentive).

Compositions in some embodiments may comprise a crystallization inhibitor(s). Exemplary crystallization inhibitors include acrylic copolymers, polyethylene glycol, polyethylene glycol hydrogenated castor oil, and any combination thereof. The crystallization inhibitor may be present, for example, at a concentration from about 1% to about 10% by weight of the composition.

Compositions in some embodiments may comprise one or more viscosity modifying agents and/or seed flowability agents. Examples of viscosity modifying agents include humic acid salts, fulvic acid salts, humin, and lignin salts, such as the sodium or potassium salt of humic acid. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material.

Non-limiting examples of wax materials that can be incorporated into the liquid seed treatment composition include plant and animal-derived waxes, such as carnauba wax, candelilla wax, ouricury wax, beeswax, spermaceti, and petroleum derived waxes, such as paraffin wax. For example, in some instances, the flowability agent may comprise carnauba wax. In some instances, the flowability agent may comprise an oil, such as soybean oil.

Compositions in some embodiments may comprise one or more additional excipients that improve the adhesion of the composition to a substrate or surface, such as a plant seed or other plant material, such as to provide a successful coating of the substrate or surface or otherwise impart improved characteristics to the adhesion or coating. Other substances may be added to a composition (e.g., coloring agents) to provide a visual indication of successful coating of the substrate or surface, such as the outer surface of a plant seed or other plant material.

Compositions of the present disclosure may comprise any suitable pigment(s) or effect pigment(s). Effect pigments, which are sometimes also referred to in the art as "pearl pigments," are a class of materials that provide reflectivity, shine, and/or a pearlescent effect when applied as a coating. In some embodiments, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.), MAGNA PEARL, LUMINA and MEARLIN pigments from BASF Corporation, PHIBRO PEARL from PhibroChem, and IRIDESIUM 120 from Aakash Chemicals. In some instances, the dry powder effect pigment has a mean particle size of from about 1 to about 25 microns.

In addition to a microbial strain or isolate described herein, compositions and formulations may further comprise one or more pesticidal agents. Pesticidal agents include chemical pesticides and biopesticides or biocontrol agents. Various types of chemical pesticides include acaricides, insecticides, nematicides, fungicides, gastropodicides, herbicides, virucides, bactericides, and combinations thereof. Biopesticides or biocontrol agents may include bacteria, fungi, beneficial nematodes, and viruses that exhibit pesticidal activity. Compositions may comprise other agents for pest control, such as microbial extracts, plant growth activators, and/or plant defense agents.

Compositions in some embodiments may comprise one or more chemical acaricides, insecticides, and/or nematicides. Non-limiting examples of chemical acaricides, insecticides, and/or nematicides may include one or more carbamates, diamides, macrocyclic lactones, neonicotinoids, organophosphates, phenylpyrazoles, pyrethrins, spinosyns, synthetic pyrethroids, tetronic acids and/or tetramic acids. Non-limiting examples of chemical acaricides, insecticides and nematicides that can be useful in compositions of the present disclosure include abamectin, acrinathrin, aldicarb, aldoxycarb, alpha-cypermethrin, betacyfluthrin, bifenthrin, cyhalothrin, cypermethrin, deltamethrin, csfenvalcrate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthrin, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., Rynaxypyr), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl)methyl](2,2-difluoroethyl)amino}furan-2(5H)-one, 3,5-disubstituted-1,2,4-oxadiazole compounds, 3-phenyl-5-(thien-2-yl)-1,2,4-oxadiazole, cadusaphos, carbaryl, carbofuran, ethoprophos, thiodicarb, aldicarb, aldoxycarb, metamidophos, methiocarb, sulfoxaflor, methamidophos, cyantraniliprole and tioxazofen and combinations thereof. Additional non-limiting examples of chemical acaricides, insecticides, and/or nematicides may include one or more of abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb, and combinations thereof.

Additional non-limiting examples of acaricides, insecticides and nematicides that may be included or used in compositions may be found in Steffey and Gray, *Managing Insect Pests,* ILLINOIS AGRONOMY HANDBOOK (2008); and Niblack, *Nematodes,* ILLINOIS AGRONOMY HANDBOOK (2008), the contents and disclosures of which are incorporated herein by reference. Non-limiting examples of commercial insecticides which may be suitable for the compositions disclosed herein include CRUISER (Syngenta, Wilmington, Del.), GAUCHO and PONCHO (Gustafson, Plano, Tex.). Active ingredients in these and other commercial insecticides may include thiamethoxam, clothianidin, and imidacloprid. Commercial acaricides, insecticides, and/or nematicides may be used in accordance with a manufacturer's recommended amounts or concentrations.

According to some embodiments, compositions may comprise one or more biopesticidal microorganisms, the presence and/or output of which is toxic to an acarid, insect and/or nematode. For example, compositions may comprise one or more of *Bacillus firmus* I-1582, *Bacillus mycoides* AQ726, NRRL B-21664; *Beauveria bassiana* ATCC-74040,

*Beauveria bassiana* ATCC-74250, *Burkholderia* sp. A396 sp. nov. rinojensis, NRRL B-50319, *Chromobacterium subtsugae* NRRL B-30655, *Chromobacterium vaccinii* NRRL B-50880, *Flavobacterium* H492, NRRL B-50584, *Metarhizium anisopliae* F52 (also known as *Metarhizium anisopliae* strain 52, *Metarhizium anisopliae* strain 7, *Metarhizium anisopliae* strain 43, and/or *Metarhizium anisopliae* BIO-1020, TAE-001; deposited as DSM 3884, DSM 3885, ATCC 90448, SD 170 and ARSEF 7711), *Paecilomyces fumosoroseus* FE991, and combinations thereof.

Compositions in some embodiments may comprise one or more chemical fungicides. Non-limiting examples of chemical fungicides may include one or more aromatic hydrocarbons, benzthiadiazole, carboxylic acid amides, morpholines, phenylamides, phosphonates, thiazolidines, thiophene, quinone outside inhibitors and strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester, and 2-(2-(3-(2,6-dichlorophenyl)-1-methyl-allylideneaminooxymethyl)-phenyl)-2-methoxyimino-N-methyl-acetamide, carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandipromamid, fenehexamid, oxytetracyclin, silthiofam, and N-(6-methoxy-pyridin-3-yl) cyclopropanecarboxylic acid amide, spiroxamine, azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.D1b), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin); dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triaz- oxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a] pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A), nitrophenyl derivates (e.g., binapacryl, dicloran, dinobuton, dinocap, nitrothal-isopropyl, tecnazen). organometal compounds (e.g., fentin salts, such as fentin-acetate, fentin chloride, fentin hydroxide); sulfur-containing heterocyclyl compounds (e.g., dithianon, isoprothiolane), organophosphorus compounds (e.g., edifenphos, fosetyl, iprobenfos, phosphorus acid and its salts, pyrazophos, tolclofos-methyl), organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanates, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In an aspect, compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-A1, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole, and combinations thereof.

For additional examples of fungicides that may be included in compositions, see, e.g., Bradley, *Managing Diseases,* Illinois Agronomy Handbook (2008), the content and disclosure of which are incorporated herein by reference.

Fungicides useful for compositions in some embodiments may exhibit activity against one or more fungal plant pathogens, including but not limited to *Phytophthora, Rhizoctonia, Fusarium, Pythium, Phomopsis, Sclerotinia,* or *Phakopsora,* and combinations thereof. Non-limiting examples of commercial fungicides which may be suitable for the compositions include PROTÉGÉ, RIVAL or ALLEGIANCE FL or LS (Gustafson, Plano, Tex.), WARDEN RTA (Agrilance, St. Paul, Minn.), APRON XL, APRON MAXX RTA or RFC, MAXIM 4FS or XL (Syngenta, Wilmington, Del.), CAPTAN (Arvesta, Guelph, Ontario) and PROTREAT (Nitragin Argentina, Buenos Ares, Argentina). Active ingredients in these and other commercial fungicides include, but are not limited to, fludioxonil, mefenoxam, azoxystrobin and metalaxyl. Commercial fungicides may be used in accordance with a manufacturer's recommended amounts or concentrations.

According to some embodiments, compositions may comprise one or more biopesticidal microorganisms, the presence and/or output of which is toxic to at least one fungus, bacteria, or both. For example, compositions may comprise one or more of *Ampelomyces quisqualis* AQ 10® (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus pumilus* AQ717 (NRRL B-21662), *Bacillus pumilus* NRRL B-30087, *Bacillus* AQ175 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* FZB42, *Bacillus amyloliquefaciens* NRRL B-50349, *Bacillus amyloliquefaciens* TJ1000 (also known as 1BE, isolate ATCC BAA-390), *Bacillus subtilis* ATCC 55078, *Bacillus subtilis* ATCC 55079, *Bacillus thuringiensis* AQ52 (NRRL B-21619), *Candida oleophila* I-182 (e.g., ASPIRE® from Ecogen Inc., USA), *Candida saitoana* BIOCURE® (in mixture with lysozyme; BASF, USA) and BIOCOAT® (ArystaLife Science, Ltd., Cary, N.C.), *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachlinensis* (e.g., REGALIA® from Marrone Bio-Innovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660; DE-THATCH-9®, DECOMP-9® and THATCH CONTROL®, Idaho Research Foundation, USA), *Streptomyces* WYE 53 (ATCC 55750; DE-THATCH-9®, DECOMP-9® and THATCH CONTROL®, Idaho Research Foundation, USA), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, der Firma BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; TRICHODERMA 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E.P.L.A.C., Brazil), *Trichoderma virens* GL-21 (SOILGARD®, Certis LLC, USA), *Trichoderma virens* G1-3 (ATCC 57678), *Trichoderma virens* G1-21 (Thermo Trilogy Corporation, Wasco, Calif.), *Trichoderma virens* G1-3 and *Bacillus amyloliquefaciens* FZB24, *Trichoderma virens* G1-3 and *Bacillus amyloliquefaciens* NRRL B-50349, *Trichoderma virens* G1-3 and *Bacillus amyloliquefaciens* TJ1000, *Trichoderma virens* G1-21 and *Bacillus amyloliquefaciens* FZB24, *Trichoderma virens* G1-21 and *Bacillus amyloliquefaciens* NRRL B-50349, *Trichoderma virens* G1-21 and *Bacillus amyloliquefaciens* TJ1000, *Trichoderma viride* TRIECO® (Ecosense Labs. (India) Pvt. Ltd., India, BIO-CURE® F from T. Stanes & Co. Ltd., Indien), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ), and combinations thereof.

Compositions in some embodiments may comprise one or more chemical gastropodicides. Non-limiting examples of chemical gastropodicides include one or more iron phosphates, metaldehydes, methiocarbs and/or salts. Examples of commercial gastropodicides that may be useful in compositions include DEADLINE® M-Ps™, MESUROL PRO®, MESUROL 75-W®, METAREX®, SLUGGO®, and combinations thereof. Additional examples of gastropodicides that can be included in compositions of the present disclosure can be found in Capinera, Handbook of Vegetable Pests (2001), the content and disclosure of which is incorporated herein by reference. Commercial gastropodicides may be used in accordance with a manufacturer's recommended amounts and concentrations.

Compositions in some embodiments may comprise one or more chemical herbicides. The herbicides may be a pre-emergent herbicide, a post-emergent herbicide, or a combination thereof. Non-limiting examples of chemical herbicides may comprise one or more acetyl CoA carboxylase (ACCase) inhibitors, acetolactate synthase (ALS) inhibitors, acetanilides, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate synthase (EPSPS) inhibitors, glutamine synthetase inhibitors, dihydropteroate synthetase inhibitors, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof. Non-limiting examples of chemical herbicides that can be useful in compositions of the present disclosure include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diflufenican, diuron, dithiopyr, ethofumesate, fenoxaprop, foramsulfron, fluazifop, fluazifop-P, flufenacet, fluometuron, flufenpyr-ethyl, flumiclorac, flumiclorac-pentyl, flumioxazin, fluoroglycofen, fluthiacet-methyl, fomesafen, fomesafen, glyphosate, glufosinate, halosulfuron, haloxyfop, hexazinone, iodosulfuron, indaziflam, imazamox, imazaquin, imazethapyr, ioxynil, isoproturon, isoxaflutole, lactofen, linuron, mecoprop, mecoprop-P, mesosulfuron, mesotrion, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, propoxycarbazone, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thiencarbazone-methyl, thenylchlor, tralkoxydim, triclopyr, trietazine, trifloxysulfuron, tropramezone, salts and esters thereof; racemic mixtures and resolved isomers thereof and combinations thereof. In an aspect, compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D, and combinations thereof.

Additional examples of herbicides that may be included in compositions in some embodiments may be found in Hager, *Weed Management*, Illinois Agronomy Handbook (2008); and Loux et al., Weed Control Guide for Ohio, Indiana and Illinois (2015), the contents and disclosures of which are incorporated herein by reference. Commercial herbicides may be used in accordance with a manufacturer's recommended amounts or concentrations.

Compositions in some embodiments may comprise one or more virucides.

According to some embodiments, compositions may comprise one or more biopesticidal or herbicidal microorganisms, the presence and/or output of which is toxic to at least one insect, plant (weed), or phytopathogenic virus, as the case may be.

Additional examples of biopesticides that may be included or used in compositions may be found in Burges, supra; Hall & Menn, Biopesticides: Use and Delivery (Humana Press) (1998); McCoy et al., Entomogenous fungi, in CRC Handbook of Natural Pesticides. Microbial Pesticides, Part A. Entomogenous Protozoa and Fungi (C. M. Inoffo, ed.), Vol. 5:151-236 (1988); Samson et al., Atlas of Entomopathogenic Fungi (Springer-Verlag, Berlin) (1988); and deFaria and Wraight, *Mycoinsecticides and Mycoacaricides: A comprehensive list with worldwide coverage and international classification of formulation types*, Biol. Control (2007), the contents and disclosures of which are incorporated herein by reference. In certain embodiments, a biocontrol microbe may comprise a bacterium of the genus *Actinomycetes, Agrobacterium, Arthrobacter, Alcaligenes, Aureobacterium, Azobacter, Bacillus, Beijerinckia, Brevibacillus, Burkholderia, Chromobacterium, Clostridium, Clavibacter, Comamonas, Corynebacterium, Curtobacterium, Enterobacter, Flavobacterium, Gluconobacter, Hydrogenophaga, Klebsiella, Methylobacterium, Paenibacillus, Pasteuria, Photorhabdus, Phyllobacterium, Pseudomonas, Rhizobium, Serratia, Sphingobacterium, Stenotrophomonas, Variovorax,* and *Xenorhabdus*, or any combination thereof. According to some embodiments, a biopesticidal microbe may include one or more of *Bacillus amyloliquefaciens, Bacillus cereus, Bacillus firmus, Bacillus, lichenformis, Bacillus pumilus, Bacillus sphaericus, Bacillus subtilis, Bacillus thuringiensis, Chromobacterium suttsuga, Pasteuria penetrans, Pasteuria usage,* and *Pseudomona fluorescens*. According to some embodiments, a biopesticidal microbe may comprise a fungus of the genus *Alternaria, Ampelomyces, Aspergillus, Aureobasidium, Beauveria, Colletotrichum, Coniothyrium, Gliocladium, Metarhizium, Muscodor, Paecilomyces, Trichoderma, Typhula, Ulocladium,* and *Verticillium*. In another aspect a fungus is *Beauveria bassiana, Coniothyrium minitans, Gliocladium virens, Muscodor albus, Paecilomyces lilacinus,* or *Trichoderma polysporum*.

A composition in some embodiments may comprise one or more biocidal agents. A biocidal component may be included or used to prevent fungal and/or bacterial growth in the composition, particularly when the composition is placed in storage. Examples of biocidal agents include dichlorophen or benzyl alcohol hemiformal based compounds, benzoisothiazolinones and rhamnolipids. Non-limiting examples of commercially available biocidal agents include ACTICIDE (THOR), PROXEL (Arch Chemical), and ZONIX (Jeneil).

In addition to a microbial strain or isolate of the present disclosure, compositions and formulations may further comprise one or more agriculturally beneficial agents, such as biostimulants, nutrients, plant signal molecules, or biologically active agents.

According to some embodiments, compositions may comprise one or more beneficial biostimulants. Biostimulants may enhance metabolic and/or physiological processes such as respiration, photosynthesis, nucleic acid uptake, ion uptake, nutrient delivery, or a combination thereof. Non-limiting examples of biostimulants that may be included or used in compositions may include seaweed extracts (e.g., ascophyllum nodosum), bacterial extracts (e.g., extracts of one or more diazotrophs, phosphate-solubilizing microorganisms and/or biopesticides), fungal extracts, humic acids (e.g., potassium humate), fulvic acids, myo-inositol, and/or glycine, and any combinations thereof. According to some embodiments, the biostimulants may comprise one or more *Azospirillum* extracts (e.g., an extract of media comprising *A. brasilense* INTA Az-39), one or more *Bradyrhizobium* extracts (e.g., an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-50611, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C), one or more Rhizobium extracts (e.g., an extract of media comprising *R. leguminosarum* SO12A-2), one or more *Sinorhizobium* extracts (e.g., an extract of media comprising *S. fredii* CCBAU114 and/or *S. fredii* USDA 205), one or more *Penicillium* extracts (e.g., an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, *P. brevicompactum* AgRF18, *P. canescens* ATCC 10419, *P. expansum* ATCC 24692, *P. expansum* YT02, *P. fellatanum* ATCC 48694, *P. gaestrivorus* NRRL 50170, *P. glabrum* DAOM 239074, *P. glabrum* CBS 229.28, *P. janthinellum* ATCC 10455, *P. lanosocoeruleum* ATCC 48919, *P. radicum* ATCC 201836, *P. radicum* FRR 4717, *P. radicum* FRR 4719, *P. radicum* N93/47267 and/or *P. raistrickii* ATCC 10490), one or more *Pseudomo-* nas extracts (e.g., an extract of media comprising *P. jessenii* PS06), one or more acaricidal, insecticidal and/or nematicidal extracts (e.g., an extract of media comprising *Bacillus firmus* I-1582, *Bacillus mycoides* AQ726, NRRL B-21664; *Beauveria bassiana* ATCC-74040, *Beauveria bassiana* ATCC-74250, *Burkholderia* sp. A396 sp. nov. rinojensis, NRRL B-50319, *Chromobacterium subtsugae* NRRL B-30655, *Chromobacterium vaccinii* NRRL B-50880, *Flavobacterium* H492, NRRL B-50584, *Metarhizium anisopliae* F52 (also known as *Metarhizium anisopliae* strain 52, *Metarhizium anisopliae* strain 7, *Metarhizium anisopliae* strain 43 and *Metarhizium anisopliae* BIO-1020, TAE-001; deposited as DSM 3884, DSM 3885, ATCC 90448, SD 170 and ARSEF 7711) and/or *Paecilomyces fumosoroseus* FE991), and/or one or more fungicidal extracts (e.g., an extract of media comprising *Ampelomyces quisqualis* AQ 10® (Intrachem Bio GmbH & Co. KG, Germany), *Aspergillus flavus* AFLA-GUARD® (Syngenta Crop Protection, Inc., CH), *Aureobasidium pullulans* BOTECTOR® (bio-ferm GmbH, Germany), *Bacillus pumilus* AQ717 (NRRL B-21662), *Bacillus pumilus* NRRL B-30087, *Bacillus* AQ175 (ATCC 55608), *Bacillus* AQ177 (ATCC 55609), *Bacillus subtilis* AQ713 (NRRL B-21661), *Bacillus subtilis* AQ743 (NRRL B-21665), *Bacillus amyloliquefaciens* FZB24, *Bacillus amyloliquefaciens* NRRL B-50349, *Bacillus amyloliquefaciens* TJ1000 (also known as 1BE, isolate ATCC BAA-390), *Bacillus thuringiensis* AQ52 (NRRL B-21619), *Candida oleophila* I-82 (e.g., ASPIRE® from Ecogen Inc., USA), *Candida saitoana* BIO-CURE® (in mixture with lysozyme; BASF, USA) and BIOCOAT® (ArystaLife Science, Ltd., Cary, N.C.), *Clonostachys rosea* f. *catenulata* (also referred to as *Gliocladium catenulatum*) J1446 (PRESTOP®, Verdera, Finland), *Coniothyrium minitans* CONTANS® (Prophyta, Germany), *Cryphonectria parasitica* (CNICM, France), *Cryptococcus albidus* YIELD PLUS® (Anchor Bio-Technologies, South Africa), *Fusarium oxysporum* BIOFOX® (from S.I.A.P.A., Italy) and FUSACLEAN® (Natural Plant Protection, France), *Metschnikowia fructicola* SHEMER® (Agrogreen, Israel), *Microdochium dimerum* ANTIBOT® (Agrauxine, France), *Muscodor albus* NRRL 30547, *Muscodor roseus* NRRL 30548, *Phlebiopsis gigantea* ROTSOP® (Verdera, Finland), *Pseudozyma flocculosa* SPORODEX® (Plant Products Co. Ltd., Canada), *Pythium oligandrum* DV74 (POLYVERSUM®, Remeslo SSRO, Biopreparaty, Czech Rep.), *Reynoutria sachlinensis* (e.g., REGALIA® from Marrone BioInnovations, USA), *Streptomyces* NRRL B-30145, *Streptomyces* M1064, *Streptomyces galbus* NRRL 30232, *Streptomyces lydicus* WYEC 108 (ATCC 55445), *Streptomyces violaceusniger* YCED 9 (ATCC 55660; DE-THATCH-9®, DECOMP-9® and THATCH CONTROL®, Idaho Research Foundation, USA), *Streptomyces* WYE 53 (ATCC 55750; DE-THATCH-9®, DECOMP-9® and THATCH CONTROL®, Idaho Research Foundation, USA), *Talaromyces flavus* V117b (PROTUS®, Prophyta, Germany), *Trichoderma asperellum* SKT-1 (ECO-HOPE®, Kumiai Chemical Industry Co., Ltd., Japan), *Trichoderma atroviride* LC52 (SENTINEL®, Agrimm Technologies Ltd, NZ), *Trichoderma harzianum* T-22 (PLANTSHIELD®, der Firma BioWorks Inc., USA), *Trichoderma harzianum* TH-35 (ROOT PRO®, from Mycontrol Ltd., Israel), *Trichoderma harzianum* T-39 (TRICHODEX®, Mycontrol Ltd., Israel; TRICHODERMA 2000®, Makhteshim Ltd., Israel), *Trichoderma harzianum* ICC012 and *Trichoderma viride* TRICHOPEL (Agrimm Technologies Ltd, NZ), *Trichoderma harzianum* ICC012 and *Trichoderma viride* ICC080 (REMEDIER® WP, Isagro Ricerca, Italy), *Trichoderma polysporum* and *Trichoderma harzianum* (BINAB®, BINAB Bio-Innovation AB, Sweden), *Trichoderma stromaticum* TRICOVAB® (C.E.P.L.A.C., Brazil), *Trichoderma virens* GL-21 (SOILGARD®, Certis LLC, USA), *Trichoderma virens* G1-3, ATCC 57678, *Trichoderma virens* G1-21 (Thermo Trilogy Corporation, Wasco, Calif.), *Trichoderma virens* G1-3 and *Bacillus amyloliquefaciens* FZB2, *Trichoderma virens* G1-3 and *Bacillus amyloliquefaciens* NRRL B-50349, *Trichoderma virens* G1-3 and *Bacillus amyloliquefaciens* TJ1000, *Trichoderma virens* G1-21 and *Bacillus amyloliquefaciens* FZB24, *Trichoderma virens* G1-21 and *Bacillus amyloliquefaciens* NRRL B-50349, *Trichoderma virens* G1-21 and *Bacillus amyloliquefaciens* TJ1000, *Trichoderma viride* TRIECO® (Ecosense Labs. (India) Pvt. Ltd., Indien, BIO-CURE® F from T. Stanes & Co. Ltd., Indien), *Trichoderma viride* TV1 (Agribiotec srl, Italy), *Trichoderma viride* ICC080, and/or *Ulocladium oudemansii* HRU3 (BOTRY-ZEN®, Botry-Zen Ltd, NZ)), and combinations thereof.

Compositions in some embodiments may comprise one or more biologically active ingredients. Non-limiting examples of biologically active ingredients include plant growth regulators, plant signal molecules, growth enhancers, microbial stimulating molecules, biomolecules, soil amendments, nutrients, plant nutrient enhancers, etc., such as lipo-chitooligosaccharides (LCO), chitooligosaccharides (CO), chitinous compounds, flavonoids, jasmonic acid or derivatives thereof (e.g., jasmonates), cytokinins, auxins, gibberellins, absiscic acid, ethylene, brassinosteroids, salicylates, macro- and micro-nutrients, linoleic acid or derivatives thereof, linolenic acid or derivatives thereof, karrikins, etc.) and beneficial microorganisms including various bacterial and/or fungal strains (e.g., *Rhizobium* spp., *Bradyrhizobium* spp., *Sinorhizobium* spp., *Azorhizobium* spp., *Glomus* spp., *Gigaspora* spp., *Hymenoscyphous* spp., *Oidiodendron* spp., *Laccaria* spp., *Pisolithus* spp., *Rhizopogon* spp., *Scleroderma* spp., *Rhizoctonia* spp., *Acinetobacter* spp., *Arthrobacter* spp, *Arthrobotrys* spp., *Aspergillus* spp., *Azospirillum* spp, *Bacillus* spp. *Burkholderia* spp., *Candida* spp., *Chryseomonas* spp., *Enterobacter* spp., *Eupenicillium* spp., *Exiguobacterium* spp., *Klebsiella* spp., *Kluyvera* spp., *Microbacterium* spp., *Mucor* spp., *Paecilomyces* spp., *Paenibacillus* spp., *Penicillium* spp., *Pseudomonas* spp., *Serratia* spp., *Stenotrophomonas* spp., *Streptomyces* spp., *Streptosporangium* spp., *Swaminathania* spp., *Thiobacillus* spp., *Torulospora* spp., *Vibrio* spp., *Xanthobacter* spp., *Xanthomonas* spp., etc.), and combinations thereof.

Non-limiting examples of fungi that may be included in compositions of the present disclosure include *Gliocladium virens* ATCC 52045, *Gliocladium virens* GL-21, *Glomus intraradices* RTI-801, *Metarhizium anisopliae* F52, PENI, *Trichoderma asperellum* SKT-1, *Trichoderma asperellum* ICC 012, *Trichoderma atroviride* LC52, *Trichoderma atroviride* CNCM 1-1237, *Trichoderma fertile* JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma viridae* ATCC 52440, *Trichoderma viridae* ICC080, *Trichoderma viridae* TV1 and combinations thereof, as well as microorganisms having at least at least 75, 80, 85, 90, 95, 96, 97, 97.5. 98, 98.5, 99, 99.5, 99.6, 99.7, 99.8, or 99.9% or greater sequence identity to any of the aforementioned fungal strains, on the basis of internal transcribed spacer (ITS) and/or cytochrome c oxidase (CO1) sequence identity.

Non-limiting examples of mycorrhizal fungi that may be included in compositions of the present disclosure include mycorrhizal strains, such as *Gigaspora margarita, Glomus aggregatum, Glomus brasilianum, Glomus clarum, Glomus deserticola, Glomus etunicatum, Glomus intraradices, Glomus monosporum, Glomus mosseae, Laccaria bicolor, Laccaria laccata, Paraglomus brazilianum, Pisolithus tinctorius, Rhizopogon amylopogon, Rhizopogon fulvigleba, Rhizopogon luteolus, Rhizopogon villosuli, Scleroderma cepa* and *Scleroderma citrinum,* and combinations thereof.

Compositions in some embodiments may comprise one or more lipo-chitooligosaccharides (LCOs), chitooligosaccharides (COs), and/or chitinous compounds. LCOs, sometimes referred to as symbiotic nodulation (Nod) signals (or Nod factors) or as Myc factors, consist of an oligosaccharide backbone of β-1,4-linked N-acetyl-D-glucosamine ("GlcNAc") residues with an N-linked fatty acyl chain condensed at the non-reducing end. As understood in the art, LCOs differ in the number of GlcNAc residues in the backbone, in the length and degree of saturation of the fatty acyl chain and in the substitutions of reducing and non-reducing sugar residues. See, e.g., Denarie et al., *Ann. Rev. Biochem.* 65:503 (1996); Diaz et al., *Mol. Plant-Microbe Interactions* 13:268 (2000); Hungria et al., *Soil Biol. Biochem.* 29:819 (1997); Hamel et al., *Planta* 232:787 (2010); and Prome et al., *Pure & Appl. Chem.* 70(1):55 (1998), the contents and disclosures of which are incorporated herein by reference.

LCOs may be synthetic or obtained from any suitable source. See, e.g., WO 2005/063784, WO 2007/117500 and WO 2008/071674, the contents and disclosures of which are incorporated herein by reference. In some aspects, a synthetic LCO may have the basic structure of a naturally occurring LCO but contains one or more modifications or substitutions, such as those described in Spaink, *Crit. Rev. Plant Sci.* 54:257 (2000). LCOs and precursors for the construction of LCOs (e.g., COs, which may themselves be useful as a biologically active ingredient) can be synthesized by genetically engineered organisms. See, e.g., Samain et al., *Carbohydrate Res.* 302:35 (1997); Cottaz et al., *Meth. Eng.* 7(4):311 (2005); and Samain et al., *J. Biotechnol.* 72:33 (1999) (e.g., FIG. 1 therein, which shows structures of COs that can be made recombinantly in *E. coli* harboring different combinations of genes nodBCHL), the contents and disclosures of which are incorporated herein by reference.

LCOs (and derivatives thereof) may be included or utilized in compositions in various forms of purity and can be used alone or in the form of a culture of LCO-producing bacteria or fungi. For example, OPTIMIZE® (commercially available from Monsanto Company (St. Louis, Mo.)) contains a culture of *Bradyrhizobium japonicum* that produces LCO. Methods to provide substantially pure LCOs include removing the microbial cells from a mixture of LCOs and the microbe, or continuing to isolate and purify the LCO molecules through LCO solvent phase separation followed by HPLC chromatography as described, for example, in U.S. Pat. No. 5,549,718. Purification can be enhanced by repeated HPLC and the purified LCO molecules can be freeze-dried for long-term storage. According to some embodiments, the LCO(s) included in compositions of the present disclosure is/are at least 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or 100% pure. Compositions and methods described herein may comprise analogues, derivatives, hydrates, isomers, salts and/or solvates of LCOs. LCOs may be incorporated into compositions of the present disclosure in any suitable amount(s)/concentration(s). For example, compositions of the present disclosure comprise about $1 \times 10^{-20}$ M to about $1 \times 10^{-1}$ M LCO(s). For example, compositions of the present disclosure can comprise about $1 \times 10^{-20}$ M, $1 \times 10^{-19}$ M, $1 \times 10^{-18}$ M, $1 \times 10^{-17}$ M, $1 \times 10^{-16}$ M, $1 \times 10^{-15}$ M, $1 \times 10^{-14}$ M, $1 \times 10^{-13}$ M, $1 \times 10^{-12}$ M, $1 \times 10^{-11}$ M, $1 \times 10^{-10}$ M, $1 \times 10^{-9}$ M, $1 \times 10^{-8}$ M, $1 \times 10^{-7}$ M, $1 \times 10^{-6}$ M, $1 \times 10^{-5}$ M, $1 \times 10^{-4}$ M, $1 \times 10^{-3}$ M, $1 \times 10^{-2}$ M, or $1 \times 10^{-1}$ M of one or more LCOs. In an aspect, the LCO concentration is $1 \times 10^{-14}$ M to $1 \times 10^{-5}$ M, $1 \times 10^{-12}$ M to $1 \times 10^{-6}$ M, or $1 \times 10^{-10}$ M to $1 \times 10^{-7}$ M. In an aspect, the LCO concentration is $1 \times 10^{-14}$ M to $1 \times 10^{-5}$ M, $1 \times 10^{-12}$ M to $1 \times 10^{-6}$ M, or $1 \times 10^{-10}$ M to $1 \times 10^{-7}$ M. The amount/concentration of LCO may be an amount effective to impart a positive trait or benefit to a plant, such as to enhance the growth and/or yield of the plant to which the composition is applied. According to some embodiments, the LCO amount/concentration is not effective to enhance the yield of the plant without beneficial contributions from one or more other constituents of the composition, such as CO and/or one or more pesticides.

Compositions in some embodiments may comprise any suitable COs, perhaps in combination with one or more LCOs. COs differ from LCOs in that they lack the pendant fatty acid chain that is characteristic of LCOs. COs, sometimes referred to as N-acetylchitooligosaccharides, are also composed of GlcNAc residues but have side chain decorations that make them different from chitin molecules [$(C_8H_{13}NO_5)_n$, CAS No. 1398-61-4] and chitosan molecules [$(C_5H_{11}NO_4)_n$, CAS No. 9012-76-4]. See, e.g., D'Haeze et al., *Glycobiol.* 12(6):79R (2002); Demont-Caulet et al., *Plant Physiol.* 120(1):83 (1999); Hanel et al., *Planta* 232: 787 (2010); Muller et al., *Plant Physiol.* 124:733 (2000); Robina et al., *Tetrahedron* 58:521-530 (2002); Rouge et al., Docking of Chitin Oligomers and Nod Factors on Lectin Domains of the LysM-RLK Receptors in the Medicago-Rhizobium Symbiosis, in The Molecular Immunology of Complex Carbohydrates-3 (Springer Science, 2011); Van der Holst et al., *Curr. Opin. Struc. Biol.* 11:608 (2001); and Wan et al., *Plant Cell* 21:1053 (2009), the contents and disclosures of which are incorporated by reference. COs may be obtained from any suitable source. For example, the CO may be derived from an LCO. For example, in an aspect, compositions of the present disclosure comprise one or more COs derived from an LCO obtained (i.e., isolated and/or purified) from a strain of *Azorhizobium, Bradyrhizobium* (e.g., *B. japonicum*), *Mesorhizobium, Rhizobium* (e.g., *R. leguminosarum*), *Sinorhizobium* (e.g., *S. meliloti*), or mycorhizzal fungi (e.g., *Glomus intraradicus*). Alternatively, the CO may be synthetic. Methods for the preparation of recombinant COs are known in the art. See, e.g., Cottaz et al., *Meth. Eng.* 7(4):311 (2005); Samain et al., *Carbohydrate Res.* 302:35 (1997.); and Samain et al., *J. Biotechnol.* 72:33 (1999), the contents and disclosures of which are incorporated herein by reference.

COs (and derivatives thereof) may be included or utilized in compositions in some embodiments in various forms of purity and can be used alone or in the form of a culture of CO-producing bacteria or fungi. According to some embodiments, the CO(s) included in compositions may be at least 0.1%, 0.5%, 1%, 2%, 3%, 4%, 5%, 6%, 7%, 8%, 9%, 10%, 15%, 20%, 30%, 40%, 50%, 60%, 70%, 75%, 80%, 85%, 90%, 91%, 92%, 93%, 94%, 95%, 96%, 97%, 98%, 99%, 99.5% or more pure. It is to be understood that compositions and methods of the present disclosure can comprise hydrates, isomers, salts and/or solvates of COs. COs may be incorporated into compositions of the present disclosure in any suitable amount(s)/concentration(s). For example, compositions of the present disclosure may comprise about $1\times10^{-20}$ M to about $1\times10^{-1}$ M COs, such as about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, or $1\times10^{-1}$ M of one or more COs. For example, the CO concentration may be $1\times10^{-14}$ M to $1\times10^{-5}$ M, $1\times10^{-12}$ M to $1\times10^{-6}$ M, or $1\times10^{-10}$ M to $1\times10^{-7}$ M. The amount/concentration of CO may be an amount effective to impart or confer a positive trait or benefit to a plant, such as to enhance the soil microbial environment, nutrient uptake, or increase the growth and/or yield of the plant to which the composition is applied. According to some embodiments, a CO amount/concentration may not be effective to enhance the growth of the plant without beneficial contributions from one or more other ingredients of the composition, such as LCO and/or one or more inoculants, biomolecules, nutrients, or pesticides.

Compositions in some embodiments may comprise one or more suitable chitinous compounds, such as, for example, chitin (IUPAC: N-[5-[[3-acetylamino-4,5-dihydroxy-6-(hydroxymethyl)oxan-2yl]methoxymethyl]-2-[[5-acetylamino-4,6-dihydroxy-2-(hydroxymethyl)oxan-3-yl]methoxymethyl]-4-hydroxy-6-(hydroxymethyl)oxan-3-ys] ethanamide), chitosan (IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol), and isomers, salts and solvates thereof.

Chitins and chitosans, which are major components of the cell walls of fungi and the exoskeletons of insects and crustaceans, are composed of GlcNAc residues. Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and U.S. Pat. No. 5,965,545 (preparation from crab shells and hydrolysis of commercial chitosan); and Pochanavanich et al., *Lett. Appl. Microbiol.* 35:17 (2002) (preparation from fungal cell walls).

Deacetylated chitins and chitosans may be obtained that range from less than 35% to greater than 90% deacetylation and cover a broad spectrum of molecular weights, e.g., low molecular weight chitosan oligomers of less than 15 kD and chitin oligomers of 0.5 to 2 kD; "practical grade" chitosan with a molecular weight of about 15 kD; and high molecular weight chitosan of up to 70 kD. Chitin and chitosan compositions formulated for seed treatment are commercially available. Commercial products include, for example, ELEXA® (Plant Defense Boosters, Inc.) and BEYOND™ (Agrihouse, Inc.).

Compositions in some embodiments may comprise one or more suitable flavonoids, including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof. Flavonoids are phenolic compounds having the general structure of two aromatic rings connected by a three-carbon bridge. Classes of flavonoids are known in the art. See, e.g., Jain et al., *J. Plant Biochem. & Biotechnol.* 11:1 (2002); and Shaw et al., *Environ. Microbiol.* 11:1867 (2006), the contents and disclosures of which are incorporated herein by reference. Several flavonoid compounds are commercially available. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast. See, e.g., Ralston et al., *Plant Physiol.* 137:1375 (2005).

According to some embodiments, compositions may comprise one or more flavanones, such as one or more of butin, eriodictyol, hesperetin, hesperidin, homoeriodictyol, isosakuranetin, naringenin, naringin, pinocembrin, poncirin, sakuranetin, sakuranin, and/or sterubin, one or more flavanonols, such as dihydrokaempferol and/or taxifolin, one or more flavans, such as one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3, 4-diols (e.g., leucocyanidin, leucodelphinidin, leucofisetinidin, leucomalvidin, luecopelargonidin, leucopeonidin, leucorobinetinidin, melacacidin and/or teracacidin) and/or dimers, trimers, oligomers and/or polymers thereof (e.g., one or more proanthocyanidins), one or more isoflavonoids, such as one or more isoflavones or flavonoid derivatives (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans, roetonoids, neoflavonoids (e.g, calophyllolide, coutareagenin, dalbergichromene, dalbergin, nivetin), and/or pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin), and combinations thereof. Flavonoids and their derivatives may be included in compositions in any suitable form, including, but not limited to, polymorphic and crystalline forms. Flavonoids may be included in compositions in any suitable amount(s) or concentration(s). The amount/concentration of a flavonoid(s) may be an amount effective to impart a benefit to a plant, which may be indirectly through activity on soil microorganisms or other means, such as to enhance plant nutrition and/or yield. According to some embodiments, a flavonoid amount/concentration may not be effective to enhance the nutrition or yield of the plant without the beneficial contributions from one or more other ingredients of the composition, such as LCO, CO, and/or one or more pesticides.

Compositions in some embodiments may comprise one or more suitable non-flavonoid nod-gene inducer(s), including, but not limited to, jasmonic acid ([1R-[1α,2β(Z)]]-3-oxo-2-(pentenyl)cyclopentaneacetic acid; JA), linoleic acid ((Z,Z)-9,12-Octadecadienoic acid) and/or linolenic acid ((Z,Z,Z)-9,12,15-octadecatrienoic acid), and analogues, derivatives, hydrates, isomers, polymers, salts and solvates thereof. Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae, Gibbrella fujikuroi*), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood et al., PLANT PHYSIOL. BIOCHEM. 44(11):759 (2006); Mabood et al., AGR. J. 98(2):289 (2006); Mabood et al., FIELD CROPS RES. 95(2-3):412 (2006); and Mabood & Smith, *Linoleic and linolenic acid induce the expression of nod genes in Bradyrhizobium japonicum* USDA 3, PLANT BIOL. (2001).

Derivatives of jasmonic acid, linoleic acid, and linolenic acid that may be included or used in compositions include esters, amides, glycosides and salts thereof. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are each independently: a hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent, such as dicyclohexyl carbodiimide (DCC), under neutral conditions. Suitable salts of linoleic acid, linolenic acid and jasmonic acid include, for example, base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing a solution of linoleic acid, linolenic acid, or jasmonic acid with a solution of the base. The salts may be precipitated from solution and collected by filtration, or may be recovered by other means such as by evaporation of the solvent.

Non-flavonoid nod-gene inducers may be incorporated into compositions in some embodiments in any suitable amount(s)/concentration(s). For example, the amount/concentration of non-flavonoid nod-gene inducers may be an amount effective to impart or confer a positive trait or benefit to a plant, such as to enhance the growth and/or yield of the plant to which the composition is applied. According to some embodiments, the amount/concentration of non-flavonoid nod-gene inducers may not be effective to enhance the growth and/or yield of the plant without beneficial contributions from one or more other ingredients of the composition, such as a LCO, CO and/or one or more pesticides.

Compositions in some embodiments may comprise karrakins, including but not limited to 2H-furo[2,3-c]pyran-2-ones, as well as analogues, derivatives, hydrates, isomers, polymers, salts and solvates thereof. Examples of biologically acceptable salts of karrakins include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Karrakins may be incorporated into compositions in any suitable amount(s) or concentration(s). For example, the amount/concentration of a karrakin may be an amount or concentration effective to impart or confer a positive trait or benefit to a plant, such as to enhance the growth and/or yield of the plant to which the composition is applied. In an aspect, a karrakin amount/concentration may not be effective to enhance the growth and/or yield of the plant without beneficial contributions from one or more other ingredients of the composition, such as a LCO, CO and/or one or more pesticides.

In some embodiments, a composition of the present disclosure may comprise one or more humic acids (e.g., one or more leonardite humic acids, lignite humic acids, peat humic acids and water-extracted humic acids). In some embodiments, a composition may comprise ammonium humate, boron humate, potassium humate and/or sodium humate. In some embodiments, one or more of ammonium humate, boron humate, potassium humate and sodium humate is/are excluded from a composition of the present disclosure. Non-limiting examples of humic acids that may be useful in embodiments of the present disclosure include MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7, and CAS Number 308067-45-0. In some embodiments, a composition of the present disclosure may comprise one or more fulvic acids (e.g., one or more leonardite fulvic acids, lignite fulvic acids, peat fulvic acids and/or water-extracted fulvic acids). In some embodiments, a composition may comprise ammonium fulvate, boron fulvate, potassium fulvate and/or sodium fulvate. In some embodiments, one or more of ammonium fulvate, boron fulvate, potassium fulvate and sodium fulvate is/are excluded from a composition of the present disclosure. Non-limiting examples of fulvic acids that may be useful in embodiments of the present disclosure include MDL Number MFCD09838488 (CAS Number 479-66-3). In some embodiments, a composition of the present disclosure may comprise one or more betaines (e.g., trimethylglycine). In some embodiments, a composition of the present disclosure may comprise one or more peptones (e.g., bacterial peptones, meat peptones, milk peptones, vegetable peptones and yeast peptones).

In some embodiments, a composition of the present disclosure may comprise one or more hygroscopic polymers (e.g., hygroscopic agars, albumins, alginates, carrageenans, celluloses, gums (e.g., cellulose gum, guar gum, gum arabic, gum combretum, xantham gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches). Non-limiting examples of polymers include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, Del.), EASYSPERSE™ polymers (Ashland Specialty Ingredients, Wilmington, Del.); DISCO™ AG polymers (e.g., L-250, L-280, L-285, L-286, L-320, L-323, L-517, L-519, L-520, L800; Incotec Inc., Salinas, Calif.), KELZAN® polymers (Bri-Chem Supply Ltd., Calgary, Alberta, Calif.), SEEDWORX™ polymers (e.g., Bio 200; Aginnovation, LLC, Walnut Groove, Calif.), TICAXAN® xanthan powders, such as PRE-HY-DRATED® TICAXAN® Rapid-3 Powder (TIC Gums, White Marsh, Md.) and combinations thereof. Additional examples of polymers may be found in Pouci, et al. AM. J. AGRIC. BIOL. SCI. 3(1):299 (2008).

Compositions in some embodiments may comprise one or more anthocyanidins and/or anthoxanthins, such as one or more of cyanidin, delphinidin, malvidin, pelargonidin, peonidin, petunidin, flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin), and combinations thereof.

Compositions in some embodiments may comprise gluconolactone and/or an analogue, derivative, hydrate, isomer, polymer, salt and/or solvate thereof. Gluconolactone may be incorporated into compositions in any suitable amount(s)/concentration(s). For example, the amount/concentration of a gluconolactone amount/concentration may be an amount effective to impart or confer a positive trait or benefit to a plant, such as to enhance the growth and/or yield of the plant to which the composition is applied. In an aspect, the gluconolactone amount/concentration may not be effective to enhance the growth and/or yield of the plant without beneficial contributions from one or more other ingredients of the composition, such as a LCO, CO and/or one or more pesticides.

In addition to a microbial strain or isolate, compositions and formulations may comprise one or more suitable nutrient(s) and/or fertilizer(s), such as organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K.), and/or carotenoids (α-carotene, β-carotene, cryptoxanthin, lutein, lycopene, zeaxanthin, etc.), and combinations thereof. In an aspect, compositions of the present disclosure may comprise macro- and micronutrients of plants or microbes, including phosphorous, boron, chlorine, copper, iron, manganese, molybdenum and/or zinc. According to some embodiments, compositions may comprise one or more beneficial micronutrients. Non-limiting examples of micronutrients for use in compositions described herein may include vitamins, (e.g., vitamin A, vitamin B complex (i.e., vitamin B1, vitamin B2, vitamin B3, vitamin B5, vitamin B6, vitamin B7, vitamin B8, vitamin B9, vitamin B12, choline) vitamin C, vitamin D, vitamin E, vitamin K, carotenoids (α-carotene, β-carotene, cryptoxanthin, lutein, lycopene, zeaxanthin, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), organic acids (e.g., acetic acid, citric acid, lactic acid, malic aclid, taurine, etc.), and combinations thereof. In a particular aspect, compositions may comprise phosphorous, boron, chlorine, copper, iron, manganese, molybdenum, and/or zinc, and combinations thereof. For compositions comprising phosphorous, it is envisioned that any suitable source of phosphorous may be used. For example, phosphorus may be derived from a rock phosphate source, such as monoammonium phosphate, diammonium phosphate, monocalcium phosphate, super phosphate, triple super phosphate, and/or ammonium polyphosphate, an organic phosphorous source, or a phosphorous source capable of solubilization by one or more microorganisms (e.g., *Penicillium bilaiae*).

According to another broad aspect, compositions are provided comprising a plant, plant part, or plant seed having a microbial strain or isolate described herein associated with, or applied to, the plant, plant part, or plant seed. According to embodiments described herein, a plant or crop plant that may be treated or associated with compositions or formulations may include a variety of monocotyledonous (monocot) and dicotyledonous (dicot) agricultural plants. Examples may include row or cereal crops, such as maize (corn), wheat, rice, barley, oat, sorghum, other cereals, soybean, cotton, canola, sugar beets, alfalfa, and vegetables. Further examples include: Amaranthaceae (e.g., chard, spinach, sugar beet, quinoa), Asteraceae (e.g., artichoke, asters, chamomile, chicory, chrysanthemums, dahlias, daisies, echinacea, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or Zoysia), millet, oats, ornamental grasses, rice, rye, sorghum, sugar cane, triticale, wheat and other cereal crops, Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, petunia, potato, tobacco, tomato), and Vitaceae (e.g., grape). Wheat plants further include varieties of winter and spring wheat, such as hard red winter wheat, soft red winter wheat, hard white winter wheat, soft white winter wheat, Durum wheat, and hard red spring wheat. Further provided is a plant part or plant seed taken or derived from any of the foregoing plants.

As used herein, a "plant part" refers to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts may be viable, nonviable, regenerable, and/or non-regenerable, and plant parts may in some cases be developed, regenerated and/or grown into a plant, as the case may be. A "propagule" may include any plant part that is capable of growing into an entire plant, and may include, for example, cuttings, rhizomes, and tubers, depending on the particular plant species. Plant parts that may be treated or associated with a microbial composition may further include other cultured plant tissues or propagation materials, such as somatic embryos and callus, which may be regenerated, developed or grown into a plant.

A plant, plant part or plant seed may be transgenic or non-transgenic and/or contain one or more genetic changes or mutations. A "plant" refers to a plant at any stage of development including an embryo, seedling, and mature plant whether grown or developed from a seed, regenerated from a cultured tissue, or propagated in any manner.

Plants, plant parts or plant seeds that may be treated or associated with microbial compositions in some embodiments may include commercial products, such as plant seeds, sold by Monsanto Company (St. Louis, Mo.) or others, such as commercial crop seed sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEN$^{D™}$, INTACTA RR2 PRO®, VISTIVE GOLD®, and/or XTENDFLEX™ trade names.

As used herein, the phrases "associated with", "in association with", or "associated therewith" in reference to a microbial composition or strain/isolate described herein and a plant, plant part or plant seed refer to at least a juxtaposition or close proximity of the microbial composition or strain/isolate and the plant, plant part or plant seed. Such a juxtaposition may be achieved by contacting or applying a microbial composition or strain/isolate to the plant, plant part, or plant seed, such as by spraying or coating the plant, plant part, or plant seed with the microbial composition, by applying as a foliar application to one or more above-ground tissues of the plant, and/or by applying the microbial composition to the soil or growth medium at, near or surrounding the site where the plant, plant part or plant seed is planted, growing, or will be planted or grown. According to many embodiments, the microbial composition is applied as a coating to the outer surface of a plant part or plant seed, which may exist as a layer around most or all of the plant part or plant seed. According to other embodiments, the microbial composition may be applied as a foliar spray or as a soil drench or application at or near the base of a crop plant. According to some embodiments, the microbial composition may be applied at or near the site of a plant seed in (or on) the soil or ground before, simultaneously with, or after planting of the plant seed.

Plants grown from seeds treated or associated with a microbial composition in some embodiments, and/or plants treated with a microbial composition in some embodiments at any stage(s) of development, may potentially have improved agronomic traits or characteristics, such as increased growth, vigor, stress tolerance, standability, lodging resistance, and/or yield. Such plants may also have one or more other beneficial traits, such as increased or improved biomass, carbohydrate biosynthesis, chlorophyll content, cold tolerance, drought tolerance, salt tolerance, plant height, leaf length, leaf mass, leaf number, leaf surface area, leaf volume, nutrient uptake (e.g., calcium, magnesium, nitrogen, phosphorous and/or potassium uptake), rate of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, and/or stomatal conductance. The improved traits may be indirectly due to improved nutrient availability and/or soil characteristics. Such traits may be increased or improved by at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 150%, 175%, or 200% (or more) in comparison to a control plant that has not been treated with a microbial composition.

Plants grown from seeds treated or associated with a microbial composition, and/or plants treated with a microbial composition at any stage(s) of development, may have one or more improved plant yield traits or characteristics. Such improved traits may include increased yield. Such plants may have yield traits or characteristics that are improved or increased by at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 150%, 175%, or 200% (or more) in comparison to a control plant that has not been treated with a microbial composition. According to some embodiments, the yield of such plants may be increased or improved on average by at least 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, or 15 bushels per acre.

According to another aspect, methods are provided for making microbial compositions and formulations. Any suitable order of addition may be applied or used to combine a microbial strain or isolate with one or more suitable ingredients, carriers, solvents, etc. As described above, a variety of different carriers, molecules, solvents, etc., may be combined with a microbial strain or isolate to make a composition or formulation. The order of addition and the suitable combination of ingredients may depend on the ability to maintain the viability of the microbial strain or isolate in the composition or formulation during storage, distribution or use. The composition or formulation may be chosen or designed to maintain the viability, survival, stability and/or shelf-life of the microbial strain or isolate during storage, distribution, and/or placement or application in association with a plant, plant part or plant seed.

Methods are further provided for applying a microbial composition to a plant part or plant seed. A microbial composition may be applied as a coating that covers at least some, most, or all of the outer surface of the plant part or plant seed. The coating of a microbial composition may be applied as one or more layers, such as one, two, three, four, five or more layers, and may comprise at least one of a plurality of layers. Applying the microbial composition to the plant part or plant seed as a distinct layer from one or more other coating layers may allow for certain substances, such bactericides, fungicides, etc., to be separated or sequestered away from the microbial composition to improve the survival and viability of the microbial strain or isolate. The thickness of each coating may vary, such as in a range from about 1.5 to about 3.5 µm in thickness. A microbial composition may be applied to a plant part or plant seed as a liquid or powder. According to some embodiments, the microbial composition or coating may comprise from about 10 to about $1\times10^{15}$ colony-forming units (cfu's) per plant part or plant seed, such as at least $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, or $1\times10^{13}$ (or more) cfu's per plant part or plant seed.

Depending on the manner of application, a microbial composition may be an amorphous liquid or solid at 20° C., 21° C., 22° C., 23° C., 24° C., 25° C., 26° C., 27° C., 28° C., 29° C., and/or 30° C., perhaps even after drying or desiccation, and have 50%, 55%, 60%, 65%, 70%, 75%, 80%, or 85% (or more) relative humidity.

Numerous methods are known in the art for applying a liquid or powder composition or formulation to a solid surface, such as the outer surface of a plant material or seed, such as solid matrix priming, imbibition, coating, misting, spraying, such as via freeze-, spray- or spray-freeze-drying, dripping, soaking, immersing, dusting or encapsulating, which may also introduce the composition or formulation into the interior tissue(s) of a plant material, such as the interior tissue(s) of a plant part or seed. A composition may be applied using a spray nozzle or revolving disc. Spraying the composition onto a plant material or seed may be performed while agitating the material or seed in an appropriate piece of equipment, such as a tumbler or a pan granulator. Alternatively, the composition may be freeze-, spray- or spray-freeze-dried prior to application to the plant material. Batch or semi-batch systems, in which predetermined batch sizes of material and composition are delivered into a tumbler, mixer, or pan granulator, may be used, wherein a known volume of the microbial composition may be introduced into the treatment equipment at a rate that allows the plant material or seed to be applied or coated evenly.

A microbial composition in some embodiments may be applied to a plant or plant material, such as one or more plant parts or plant seeds, by any standard treatment methodology known in the art, including but not limited to those listed above and other standard or conventional methods, such as mixing in a container (e.g., a bottle or bag), mechanical application, tumbling, spraying, immersion, solid matrix priming, etc. Other conventional coating methods and machines, such as fluidized bed techniques, the roller mill method, rotostatic seed treaters, and drum coaters, may also be used. Any conventional active or inert material may be used for contacting seeds with a seed treatment composition, such as conventional film-coating materials including, but not limited to, water-based film coating materials. According to some embodiments, plant materials (e.g., plant parts or seeds) are coated by applying a composition described herein to the inside wall of a round container, adding the plant material, and rotating the container such that the material comes into contact with the composition, a process known in the art as "container coating". Continuous treatment systems, which are calibrated to apply a composition at a predefined rate in proportion to a continuous flow of material, such as plant seed, may also be employed. Seed coating methods and apparatus for their application are disclosed in, for example, U.S. Pat. Nos. 5,918,413, 5,891, 246, 5,554,445, 5,389,399, 5,107,787, 5,080,925, 4,759,945 and 4,465,017, among others, the contents and disclosures of which are incorporated herein by reference.

According to some embodiments, a composition for application to a plant or plant material, such as a plant part or seed, comprising a microbial strain or isolate may be introduced onto or into a plant material by use of solid matrix priming. For example, a quantity of the treatment composition may be mixed with a solid matrix material, and the plant material may be placed into contact with the solid matrix material for a period of time to allow the treatment composition to be introduced to the plant material. The plant material may then optionally be separated from the solid matrix material and stored or used, or a mixture of solid matrix material plus seed/plant part may be planted directly. Solid matrix materials may include polyacrylamide, starch, clay, silica, alumina, soil, sand, polyurea, polyacrylate, and/or any other material capable of absorbing or adsorbing the treatment composition for a time, and then releasing the composition into or onto the plant material. It is useful to ensure that the microbe and the solid matrix material are compatible with each other.

According to other embodiments, a plant material, such as a plant part or seed, may be treated with a microbial composition by imbibition in a treatment composition. For example, the plant material may be directly immersed for a period of time in the treatment composition. During the period of time that the plant material is immersed, the plant material may take up or become imbibed with a portion of the treatment composition. The mixture of plant material and the treatment composition may be agitated, for example by shaking, rolling, tumbling, or other means. After imbibition, the plant material may be separated from the treatment composition and optionally dried, stored and/or planted.

In some embodiments, the treated seeds may also be enveloped with a film overcoating to protect the nematicidal coating. Such overcoatings are known in the art and may be applied using conventional fluidized bed and drum film coating techniques. The overcoatings may be applied to seeds that have been treated with any of the seed treatment techniques described above, including but not limited to solid matrix priming, imbibition, coating, and spraying, or by any other seed treatment technique known in the art.

After application of a microbial composition to a plant material, such as a plant part or plant seed, the plant material may be optionally dried or partially dried.

Microbial compositions for application to the surface of a plant, plant part or plant seed may contain one or more adherents, binders, adhesives or adhesive polymers ("adherents"), such as one or more maltodextrins, gums (e.g., cellulose gum, guar gum, gum arabic, gum combretum, xantham gum), one or more mono-, di-, oligo- and/or polysaccharides, sugar alcohols, proteins, peptones, oils (e.g., mineral oil, olive oil, peanut oil, soybean oil and/or sunflower oil), and/or synthetic polymers, such as polyvinylpyrrolidone (PVP) or polyethylene glycol (PEG). Such adherents may include a paraffinic hydrocarbon solvent.

In some embodiments, a microbial composition provided herein may comprise one or more maltodextrins (e.g., one or more maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25). According to some embodiments, a microbial composition may comprise one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. According to some embodiments, a microbial composition may comprise a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. Non-limiting examples of maltodextrins include MALTRIN® M040 (DEV=5; molecular weight=3600; Grain Processing Corporation, Muscatine, Iowa), MALTRIN® M100 (DEV=10; molecular weight=1800; Grain Processing Corporation, Muscatine, Iowa), MALTRIN® M150 (DEV=15; molecular weight=1200; Grain Processing Corporation, Muscatine, Iowa), MALTRIN® M180 (DEV=18; molecular weight=1050; Grain Processing Corporation, Muscatine, Iowa), MALTRIN® M200 (DEV=20; molecular weight=900; Grain Processing Corporation, Muscatine, Iowa), MALTRIN® M250 (DEV=25; molecular weight=720; Grain Processing Corporation, Muscatine, Iowa); MALTRIN QD® M580 (DEV=16.5-19.9; Grain Processing Corporation, Muscatine, Iowa); MALTRIN QD® M585 (DEV=15.0-19.9; Grain Processing Corporation, Muscatine, Iowa); MALTRIN QD® M600 (DEV=20.0-23.0; Grain Processing Corporation, Muscatine, Iowa); GLOBE® Plus 15 DE (Ingredion Inc., Westchester, Ill.); and combinations thereof.

The amount of a microbial composition applied to the surface of a plant seed may vary, but may be in a range from about 0.05 mg of the composition per seed to about 1 mg of the composition per seed, or from about 0.05 to about 0.5 mg of the composition per seed. A microbial composition may also be applied in an amount ranging from about 0.5 to about 10 milliliters of the composition per kilogram of plant material (e.g., seed).

A microbial composition in some embodiments may be applied to a plant seed prior to sowing the seed. In this manner, seeds may be treated, for example, at a central location and then distributed for planting. This may permit a person who plants the seeds to avoid the difficulty and effort associated with handling and applying the seed treatment composition, so they can plant the treated seeds in a manner that is conventional for untreated seeds.

Drying powders (e.g., comprising magnesium stearate, magnesium sulfate, calcium stearate, attapulgite clay, montmorillonite clay, graphite, powdered milk, silica (e.g., fumed silica, hydrophobically-coated silica and/or precipitated silica), soy lecithin and/or talc) may also be used or applied in any suitable amount(s) or concentration(s), such as in an amount ranging from about 0.5 to about 10 grams of drying powder per kilogram of plant material (e.g., seed).

In some embodiments, a microbial composition may comprise one or more monosaccharides (e.g., allose, altrose, arabinose, fructose, galactose, glucose, gulose, iodose, lyxose, mannose, ribose, talose, threose and/or xylose). According to some embodiments, a microbial composition does not comprise glucose. In some embodiments, a microbial composition comprises one or more disaccharides (e.g., cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose). In some embodiments, a composition may comprise one or more oligosaccharides (e.g., fructo-oligosaccharides, galacto-oligosaccharides, mannon-oligosaccharides and/or raffinose). In some embodiments, a composition may comprise one or more sugar alcohols (e.g., arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and/or xylitol).

According to some embodiments, the microbial composition may be applied to a plant part or plant seed at least 1, 2, 3, 4, 5, 6, 7, 8, 9, 10, 11, 12, 15, 18, 21, 24, 27, 30, 33, 36, 39, 42, 45, or 48 hours or more prior to planting the plant part or plant seed. The microbial composition may also be applied to a plant part or plant seed at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, or 100 weeks or more prior to planting the plant part or plant seed. According to some embodiments, the microbial composition may be applied to a plant part or plant seed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 months or more prior to planting. According to further embodiments, the microbial composition may be applied to a plant part or plant seed at least 1, 2, 3, 4, or 5 years or more prior to planting.

According to some embodiments, a microbial composition may be one of two or more compositions or formulations that may be combined or applied separately to a plant or plant material, such as a plant part or plant seed. For example, a microbial composition or formulation may be combined with an adherent-containing composition or formulation prior to application of the combined composition/formulation to a plant material, such as a plant, plant part or plant seed. When two compositions are used, the weight or volume ratio between the two compositions may vary from about 1:20 to about 20:1, from about 1:10 to about 10:1, or about 1:5, 1:3, 1:2, 2:1, 3:1, or 5:1. The microbial composition and the additional composition may be mixed and applied to the plant material simultaneously, or one of the two or more compositions may be applied successively (i.e., the microbial composition or the additional composition may be applied first followed by the other), which may create coating layers on the plant material. For example, the additional composition may provide a protective layer around the previously applied microbial composition, or the additional composition may be applied first to improve the binding or adhesion of the microbial composition to the plant material. Two or more compositions may be mixed prior to application to the plant material if the combined compositions may cause the microbe to degrade or lose viability. According to some embodiments, a solid or dried formulation or powder comprising a microbial strain or isolate may be reconstituted in one or more liquid solvents for further formulation with other ingredients and/or application to a plant, plant part or plant seed. Microbial compositions may also be combined with a number of commercially available seed finishers, such as PERIDIAM™, PRECISE™, etc., for application of the combined composition with the seed finisher to a plant, plant part or plant seed.

Methods are further provided for applying a microbial composition to a foliar tissue of a plant or to a growth medium or soil, which may comprise application of the microbial composition to the roots or root tissue of a plant. A "growth medium" may include soil and any other medium known in the art that permits growth of a plant by providing a medium, matrix or substrate for root growth. A microbial composition may be applied to a growth medium or soil prior to planting, simultaneously with or near the time of planting, such as within the furrow, or after planting (including during later stages of plant growth). According to some embodiments, a microbial composition may be applied directly to the soil at, near or surrounding a planted seed or the root zone of a plant. According to some embodiments, a microbial composition may be applied directly to the foliar tissues (e.g., leaf/leaves, stem, etc.) of a plant.

Such application of a microbial composition to a plant or soil or growth medium may be performed using any method or apparatus known in the art, including but not limited to, a hand sprayer, mechanical sprinkler or sprayer, pressurized sprayer, injection, transplant water systems, plant/root dips, or by irrigation including drip irrigation. Indeed, the composition may be applied to a plant, seed, and/or surrounding soil or growth medium through sprays, drenching, drips, and/or other forms of liquid application.

Compositions comprising a microbial strain or isolate in some embodiments may be used to improve one or more agronomic traits of a plant. Plants grown from seeds treated or associated with a microbial composition, and/or plants treated with a microbial composition at any stage(s) of development, may potentially have improved agronomic characteristics, such as increased or improved growth, vigor, stress tolerance, emergence, standability, lodging resistance, nutrient uptake, plant nutrition, and/or yield. Improved agronomic characteristics of the plant may result indirectly from improved nutrient availability and/or soil characteristics. Accordingly, methods are provided for planting a plant seed or regenerable plant part treated or associated with a microbial composition in a field or controlled environment, and growing a plant from the treated plant seed or plant part. Alternatively, a plant seed or regenerable plant part may be planted in a field or controlled environment, and a microbial composition may be applied to the soil at or near the seed prior to, during or after planting, and/or a microbial composition may be applied to the plant at later stage(s) of development, such as via a foliar spray. According to some embodiments, methods are provided for improving one or more agronomic traits of a plant, such as increased productivity or yield, by planting a seed or plant part that has been treated with a microbial composition, or by applying a microbial composition to the soil, seed or plant either before, during or after planting, and growing, regenerating or developing a plant therefrom.

Mature plants produced by these methods may have one or more improved agronomic traits, such as increased or improved biomass, emergence, plant stand count, lodging resistance, carbohydrate biosynthesis, chlorophyll content, live green vegetation or leaves, cold tolerance, drought tolerance, salt tolerance, height, leaf length, leaf mass, leaf number, leaf surface area, leaf volume, leaf canopy, nutrient uptake (e.g., increased ammonium, calcium, magnesium, nitrogen, nitrate, phosphate, iron, manganese, phosphorous, zinc, sodium, boron, copper, sulfur and/or potassium uptake and/or presence in the leaves or other plant tissues), rate of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, and/or stomatal conductance. Such traits may be increased or improved by at least 1%, 2%, 3%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 150%, 175%, or 200% (or more) in comparison to a control plant that has not been treated with a microbial composition. Alternatively or additionally, mature plants produced by these methods may have improved performance, growth, and/or yield related to indirect effects of the microbial strain or isolate, which may be in response to improved nutrition, nutritional availability, improved soil characteristics, the presence or activity of the microbe, or microbial symbiosis.

Plants grown by methods described herein may have one or more improved plant yield traits or characteristics, such as increased yield, increased biomass, increased grain weight per plot or per plant, improved nutritional content, greater resistance to lodging, increased root length, improved plant growth or vigor, increased stress tolerance, increased harvest index, increased fresh ear weight, increased ear length, increased ear diameter, increased ear weight, increased seed number, increased seed weight, increased seed size, and/or increased bushels per acre (or per other measurement of area). Such plant yield traits or characteristics may be improved or increased by at least 1%, 2%, 3%, 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 150%, 175%, or 200% (or more) in comparison to a control plant that has not been treated with a microbial composition described herein.

According to some embodiments, methods are provided for applying or associating a microbial strain or isolate with a plant, plant part or plant seed, or to a growth medium or soil associated with a plant, plant part or plant seed, in one or more geographies or locations. A microbial strain or isolate may have a positive effect on the yield and/or stress tolerance of a plant in one or more geographies or locations, which may depend on the particular crop plant and the variable range of environmental conditions from year to year at such geographies or locations. Environmental factors that may have an impact on the yield of a plant, such as the different soil types and chemistries, weather conditions, surrounding microbiome, etc., can differ significantly between locations. Accordingly, a microbial strain or isolate may be applied to, or associated with, a plant, plant part or plant seed in one or more geographies or locations depending on its activity and effect on the characteristics of the plant, such as increased yield, stress tolerance, etc., at such geography(-ies) or location(s). Depending on the particular geography and location, a different germplasm or maturity group of the crop plant may be used. Thus, a composition comprising a microbial strain or isolate may be applied to (e.g., coated onto), or associated with, a crop plant, plant part or plant seed having the appropriate germplasm and relative maturity for the particular geography where the crop plant, plant part or plant seed will be grown or planted.

According to some embodiments, methods are provided for enhancing plant growth and/or yield of a crop plant by applying or associating a microbial strain or isolate of the present disclosure to or with a plant, plant part or plant seed, or to a growth medium or soil associated with a plant, plant part or plant seed, in one or more geographical regions, including, but not limited to, agricultural regions in Afghanistan, Argentina, Australia, Bangladesh, Belarus, Bolivia, Bosnia and Herzegovina, Brazil, Canada, Chile, China, Colombia, Congo, Ecuador, Egypt, Ethiopia, Europe (e.g., agricultural region(s) of one or more of Austria, Belgium, Bulgaria, Burma, Croatia, Czech Republic, Cyprus, Denmark, Estonia, Finland, France, Germany, Greece, Hungary, Ireland, Italy, Latvia, Lithuania, Luxembourg, Malta, Netherlands, Poland, Portugal, Romania, Slovenia, Slovakia, Spain, Sweden, Switzerland and/or United Kingdom), Iceland, India, Indonesia, Iran, Iraq, Japan, Kazakhstan, Kenya, Malawi, Mexico, Morocco, Nepal, Nigeria, Norway, Pakistan, Paraguay, Peru, Philippines, Russia, Serbia, South Africa, Taiwan, Tanzania, Thailand, Turkey, Uganda, Ukraine, Uzbekistan, Venezuela, Vietnam, Zambia, Zimbabwe, and/or the United States (e.g., agricultural region(s) of one or more of Arkansas, Colorado, Idaho, Illinois, Indiana, Iowa, Kansas, Kentucky, Louisiana, Maryland, Michigan, Minnesota, Mississippi, Missouri, Montana, Nebraska, North Carolina, North Dakota, Ohio, Oklahoma, South Dakota, Tennessee, Texas, Washington, and/or Wisconsin).

According to some embodiments, methods are provided for enhancing plant growth and/or yield of a corn or maize crop plant by applying or associating a microbial strain or isolate of the present disclosure to or with a corn or maize plant, plant part or plant seed, or to a growth medium or soil associated with a corn or maize plant, plant part or plant seed, in one or more geographical regions of the United States to increase growth and/or yield of the crop plant, such as for example, in a northern region including the agricultural region(s) of one or more of Iowa (e.g., northern Iowa), Michigan, Minnesota, South Dakota, and/or Wisconsin; in a central region including the agricultural region(s) of one or more of Illinois (e.g., northern and/or central Illinois), Indiana (e.g., northern Indiana), Iowa (e.g., southern Iowa), Ohio, and/or Nebraska (e.g., northern and/or southern Nebraska); and/or in a southern region including the agricultural region(s) of one or more of Arkansas, Illinois (e.g., southern Illinois), Indiana (e.g., southern Indiana), Kansas, Maryland, Missouri (e.g., central and/or southern Missouri), Mississippi (e.g., northern and/or southern Mississippi), Nebraska (e.g., southern Nebraska), Tennessee, and/or Texas. North Dakota may optionally also be part of the northern region; Kansas (e.g., northern Kansas) and/or Missouri (e.g., northern Missouri) may optionally also be part of the central region; Alabama (e.g., northern and/or southern Alabama), Georgia (e.g., northern and/or southern Georgia), Kansas, Kentucky, Louisiana, North Carolina, Oklahoma, South Carolina, and/or Virginia may optionally also be part of the southern region.

According to some embodiments, methods are provided for enhancing plant growth and/or yield of a wheat crop plant by applying or associating a microbial strain or isolate of the present disclosure to or with a wheat plant, plant part or plant seed, or to a growth medium or soil associated with a wheat plant, plant part or plant seed, in one or more geographical regions of the United States to increase growth and/or yield of the crop plant, such as for example, in a first northern region for spring wheat including the agricultural region(s) of one or more of North Dakota and/or optionally Minnesota, Montana (e.g., eastern Montana), Nebraska, South Dakota and/or Wyoming (e.g., eastern Wyoming); in a second northern region for spring wheat including the agricultural region(s) of Idaho, Washington and/or optionally Oregon; in a northern region for winter wheat including the agricultural region(s) of one or more of Idaho, Washington and/or optionally Oregon; in a first central region for winter wheat including the agricultural region(s) of one or more of Colorado, Nebraska and/or optionally South Dakota and/or Wyoming (e.g., eastern Wyoming); in a second central region for winter wheat including the agricultural region(s) of one or more of Illinois, Ohio and/or optionally Indiana, Iowa and/or Missouri; in a third central region for winter wheat including the agricultural region(s) of one or more of Kansas, Texas and/or optionally Oklahoma; and/or in a southern region for winter wheat including the agricultural region(s) of one or more of Texas and/or Oklahoma.

According to some embodiments, methods are provided for enhancing plant growth and/or yield of a crop plant by applying or associating a microbial strain or isolate of the present disclosure to or with a crop plant, plant part or plant seed, or to a growth medium or soil associated with a crop plant, plant part or plant seed, in one or more locations or geographies having one or more environmental properties, characteristics or growth conditions, which may vary seasonally, monthly, monthly, weekly, or daily during the year or growing season, such as higher or lower average humidity, higher or lower average rainfall amounts, wet, dry or drought conditions, and/or various soil properties and characteristics.

According to some embodiments, methods are provided for enhancing plant growth and/or yield of a crop plant by applying or associating a microbial strain or isolate of the present disclosure to or with a plant, plant part or plant seed, or to a growth medium or soil associated with a plant, plant part or plant seed, wherein the growth medium or soil associated with the plant, plant part or plant seed has one or more of the following characteristics: higher or lower (including relative amounts of) sand, silt, clay, loam and/or organic matter, fine or coarse texture, USDA soil classification, higher or lower electrical conductivity, higher or lower pH and/or pH buffering capacity, higher or lower cation exchange capacity (CEC), higher or lower aeration, higher or lower water holding capacity, higher or lower drainage, and higher or lower macro- and/or micro-nutrients, such as one or more of ammonium, nitrate, phosphate, potassium, iron, manganese, magnesium, calcium, zinc, sodium, boron, copper sulfur and/or sulfate, each in various known forms and compounds, relative to an average for such characteristic across agricultural locations or regions. A plant growth medium or soil may also be defined in terms of the measurement(s), range(s), degree(s) and/or relative amount(s) or ratio(s), including a deficit or surplus relative to what is ideal, optimal or normal for the crop plant, of any one or more of the foregoing soil properties or characteristics.

Microbial compositions of the present disclosure may be used to enhance plant growth and/or yield of a crop plant under various growth conditions, including, but not limited to, nutritional deficits (e.g., calcium, iron, manganese, magnesium, nitrogen, phosphorous, potassium and/or sulfur deficiencies), humidity extremes, pH extremes, temperature extremes, (e.g., average daytime temperatures below 60, 61, 62, 63, 64, 65, 66, 67, 68, 69, 70, 71, 72, 73 74 or 75° C., average daytime temperatures above 85, 86, 87, 88, 89, 90, 91, 92, 93, 94, 95, 96, 97, 98, 99, 100° C. or more, average nighttime temperatures below 50, 51, 52, 53, 54, 55, 56, 57, 58, 59, 60, 61, 62, 63, 64, 65, 66, 67, 68, 69 or 70° C., average nighttime temperatures above 70, 71, 72, 73, 74, 75, 76, 77, 78, 79, 80, 81, 82, 83, 84, 85° C. or more, etc.) and drought conditions (e.g., less than 5, 6, 7, 8, 9, 10, 11, 12, 13, 14 or 15 inches of rainfall during the growing season). It is to be understood that any determination of what constitutes a nutritional deficit, temperature extreme, drought condition, etc., may account for the plant species/variety being grown, as different species/varieties may have different preferences and requirements for optimal yield.

Containers and kits comprising a microbial composition are further provided comprising a microbial composition described herein. Kits may further include other compositions and instructions for using the microbial composition, such as in conjunction with farming practices. Containers may include bags or other containers or enclosures containing a dry formulation or powder of a microbial composition, and jugs or other containers may contain a liquid formulation of a microbial composition. Further provided are bags or other containers or enclosures that have seeds or other plant materials that have been treated or coated with a microbial composition.

Deposit of Biological Material

Purified cultures of the microbial strains identified herein as MON 202477 and MON 201251 were deposited with the American Type Culture Collection (ATCC), 10801 University Blvd., Manassas, Va. 20110-2209 in accordance with the Budapest Treaty for the purpose of patent procedure and the regulations thereunder (Budapest Treaty). The accession numbers for the deposited MON 202477 and MON 201251 strains are PTA-123720 and PTA-124246, respectively, which were deposited with the ATCC on Dec. 16, 2016 and Jul. 19, 2017, respectively. The microbial strain have been deposited under conditions that ensure that access to the cultures will be available during the pendency of this patent application to one determined by the Commissioner of Patents and Trademarks to be entitled thereto under 37 C.F.R. § 1.14 and 35 U.S.C. § 122. The deposits represent substantially pure cultures of the deposited strains. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Microorganisms provided herein may have one or more of the identifying characteristics of the deposited strains and, in particular, the identifying characteristics of being able to confer increased yield to plants as described herein. In some embodiments, microorganisms provided herein include the deposited microorganism, and mutants, variants or derivatives thereof.

EXAMPLES

Example 1. Sourcing and Isolation of Microbial Strains

A field testing strategy was used to identify microbes having a positive impact on yield across numerous geographical locations. Hundreds of microbial strains isolated from a variety of geographies were tested in replicate plots at multiple field locations spanning 20 U.S. states. Strains that showed significant yield enhancement across a variety of agricultural field locations were advanced for further investigation and testing.

Two microbial strains, designated MON 202477 and MON 201251, were each isolated through plant driven selection (PDS) from the rhizosphere of a corn plant grown in a controlled environment growth chamber for three weeks (until V4 stage) in soil taken from an undeveloped location in Iowa, USA. Five grams of roots with attached soil were harvested from the plant, submerged in Phosphate Buffered Saline (PBS), and sonicated to produce a microbial cell suspension. This sonicated root extract was concentrated using a centrifuge, and subsequently used to inoculate a surface-sterilized corn seed, which was then air dried and stored for seven days at room temperature prior to isolation. The microbial strains were subsequently isolated by soaking and mixing the treated seed in PBS, and then serially diluting the resulting cell suspension onto R2A medium (g/L: 0.5 casamino acids, 0.5 dextrose, 0.5 proteose peptone, 0.5 soluble starch, 0.5 yeast extract, 0.5 sodium private, 0.3 $K_2HPO_4$, 0.05 $MgSO_4.7H_2O$, 15 agar). Individual colonies that formed on the medium surface were picked and subjected to 16S sequencing for strain identification.

Example 2. Identification and Sequencing of the Microbial Strains

The MON 202477 and MON 201251 isolates were both identified as *Bacillus psychrosaccharolyticus* by 16S ribosomal DNA (rDNA) sequencing. The 16S rDNA sequences were determined by whole genome next-generation sequencing (NGS) and deduction of the relevant 16S rDNA sequence. The 16S rDNA sequences for the MON 202477 and MON 201251 isolated strains are provided as SEQ ID NO: 1 and SEQ ID NO: 2, respectively.

Example 3. Nitrate Reduction Assay for MON 201251 Strain

The MON 201251 isolate was tested in a panel of in vitro assays, and demonstrated a positive activity for nitrate reduction. A nitrate reduction test was used to indicate the ability of the isolate to perform nitrate respiration under limiting oxygen conditions. Nitrate broth (4 mL) was inoculated with a heavy inoculum (1 μL loop from pure culture on agar), distributed by vortexing, and incubated in static culture tubes at 28° C. for 24-48 h. A one mL aliquot of culture was removed to a fresh tube and BBL Nitrate Reagent A (5 drops of 0.8% sulfanilic acid in 5N acetic acid; BD Ref. 261197) and BBL Nitrate Reagent B (5 drops of 0.6% N, N-dimethyl-alpha-naphthylamine in 5N acetic acid; BD Ref. 261198) were added and immediately mixed. Pink coloration was produced within 2 minutes until zinc dust was added. This test indicated that nitrate was present, and was being reduced to nitrite by MON 201251. The MON 202477 strain, however, was not found to have a similar nitrate reduction activity (data not shown).

Example 4. Culturing and Application of Microbial Strains to Plant Seeds for Testing The isolated MON 202477 and MON 201251 microbial strains were each grown in a liquid culture medium, and then frozen in 15% glycerol prior to use. The frozen MON 202477 and MON 201251 cultures were each later thawed, diluted to a predetermined concentration, and applied to the surface of corn or wheat plant seeds to achieve a desired number of colony forming units (cfu's) per seed. The corn seeds were pretreated with base fungicides (ipconozole, metalaxyl, azoxystrobin), and the wheat seeds were pretreated with base fungicides (ipconozole, metalaxyl) and insecticides (imidacloprid). The microbial strains were applied to corn or wheat seeds in a rotating mechanical drum at an application rate to promote an even distribution of the microbe from seed to seed. After the microbe was applied to the surface of the seeds, an overtreatment mixture comprising a polymer, colorant, and water was subsequently applied to the seed to aid with sticking the microbe to the seed. After these treatment steps, the seeds were allowed to continue tumbling for another 2 minutes to dry.

Example 5. Corn Field Trials with the MON 202477 and MON 201251 Strains

Hybrid corn seeds treated (coated) with the MON 202477 or MON 201251 isolated strain were tested in multiple years of broad acre yield (BAY) trials at 48-55 field locations each year across a variety of corn growing geographies within the United States. One hybrid was used at each location in Year 1 and Year 3, and three different hybrids were used at each location in Year 2. The relative maturity of the germplasms tested in each year was matched to the geographical location (RM103, RM111, and RM113 in Year 1; RM101-103, RM110-111, and RM112-116 in Year 2; and RM95-105, RM105-110, and RM110-120 in Year 3). In Year 1 field trials, two reps were conducted at each field location, with a total of 110 plots tested per strain across all locations and germplasms (if more than one germplasm tested per location), and each plot being two rows of about 15 feet in length with a row spacing of about 30 or 38 inches (i.e., a planting density of about 34,000-36,000 plants/acre). In Year 2 field trials, three reps per germplasm were conducted at each location, with a total of 495 plots tested per strain across all locations and germplasms, and each plot being two rows of about 15 feet in length with a row spacing of about 30 inches (i.e., a planting density of about 36,000 plants/acre). Year 3 field trials were conducted with two different types of plots. In Type I (Year 3) plots, 9 reps were conducted at each location, with a total of 432 plots tested per strain across all locations and germplasms, and each plot being two rows of about 17.5 feet in length with a row spacing of about 30 inches (i.e., a planting density of about 35,000 plants/acre). In Type II (Year 3) plots, 1 rep was conducted at each location, with each rep corresponding to 460 plots, and each plot being 4 rows of 17.5 feet in length with a row spacing of about 30 inches (i.e., a planting density of about 35,000 plants/acre).

The field testing trials for broad acre yield utilized a randomized complete block design and spatial analysis. Trials contained multiple control plots that were averaged by replicate (and by germplasm when more than one germplasm was used in a trial). The effect of the microbial treatment on crop yield was compared to control plants, which were also treated with base fungicides. At harvest, yield measurements from all of the individual plots were combined, and yield was calculated using the shell weight (SHW) for corn as well as moisture (MST), according to the following formula:

$$\text{Corn yield} = ((100-\text{MST})/84.5) \times (\text{SHW}/56) \times (43560/(\text{length} \times \text{width})).$$

Unless otherwise noted, the yield deltas in Tables 1 and 2 have a p-value≤0.05.

MON 202477 was tested in corn in Year 1, Year 2 and Year 3. The data in Table 1 below provide the changes in yield (delta) with MON 202477-treated plants relative to control plants across locations for each year of testing. As shown in Table 1 below, hybrid plants grown from corn seed treated with the MON 202477 isolate had significantly increased yield in Year 1 and Year 2 testing relative to control plants. Although broad acre yield was neutral (not significantly different with a p-value=0.7) in Year 3 testing for both Type I and Type II testing plots, MON 202477 did provide a cross-year average of 2.1 bu/acre increase in yield across germplasms and geographically diverse locations. Corn seeds treated with Acceleron® were also coated with the MON 202477 isolated strain and demonstrated similar results as the other Year 3 field trials (data not shown).

TABLE 1

Corn Broad Acre Yield Increases (bushels/acre) with MON 202477

| Microbe | Year 1 | Year 2 | Year 3 (Type I) | Year 3 (Type II) |
|---|---|---|---|---|
| MON 202477 | 5.10 | 0.72 | 0.4 | −0.8 |

MON 201251 was tested in corn in Year 1 and Year 2. The data in Table 2 below provide the changes in yield (delta) of MON 201251-treated plants relative to control plants across locations for each year of testing. As shown in Table 2, hybrid plants grown from corn seeds treated with the MON 201251 isolate had increased yield in Year 1 of testing relative to control plants with a significant 3.1 bu/acre increase in yield across geographically diverse locations. Although broad acre yield was neutral (not a statistically significant change with a p-value=0.6) relative to control plants, MON 201251 did provide a positive cross-year average yield increase of about 1.4 bu/acre across all locations.

TABLE 2

Corn Broad Acre Yield Delta (bushels/acre) with MON 201251

| Microbe | Year 1 | Year 2 |
|---|---|---|
| MON 201251 | 3.1 | −0.4 |

Example 6. Wheat Field Trials with the MON 202477 and MON 201251 Strains

Spring and winter varieties of wheat seeds treated (coated) with the isolated MON 202477 or MON 201251 microbial strains were tested in 2017 in broad acre yield (BAY) trials at 10 (spring wheat) and 35 (winter wheat) field locations across a variety of wheat growing geographies in the United States. Testing locations were spread over multiple geographical zones, and different wheat varieties of the appropriate relative maturity were tested within each zone. Two spring wheat varieties and four winter wheat varieties were tested in these trials. In spring wheat field trials, four reps per variety were conducted at each field location, with a total of 40 plots tested per strain across all locations. In winter wheat field trials, two reps per variety were conducted at each location, a total of 70 plots tested per strain across all locations. In both spring wheat and winter wheat trials, each plot corresponded to seven rows of about 15 feet in length and 5 feet in width with a row spacing of about 7.5 inches (i.e., a planting density of about 750,000-1,500,000 plants/acre).

The field trials for broad acre yield utilized a randomized complete block design and spatial analysis. Trials contained multiple control plots that were averaged by replicate and by variety. The effect of the microbial treatment on crop yield was compared to control plants, which were also treated with the base fungicides and insecticides. At harvest, yield measurements from all of the individual plots were combined and yield was calculated using the harvested plot weight (HWT) for wheat as well as moisture (MST) and plot dimensions (length and width in feet), according to the following formula:

$$\text{Wheat yield} = ((100-\text{MST})/88) \times (\text{HWT}/60) \times (43560/(\text{length} \times \text{width}))$$

Unless otherwise noted in the text, the yield deltas in Table 3 have a p-value≤0.05.

Seeds of spring and winter wheat varieties were treated (coated) with the MON 202477 isolated strain and tested in broad acre yield trials. As shown in Table 3 below, no statistically significant yield increase or decrease was observed with either spring wheat or winter wheat (p-value=0.4 and 0.7, respectively). As further shown in Table 3, spring wheat varieties treated (coated) with the MON 201251 isolated strain showed neutral broad acre yield (p-value=0.6) in comparison to control plants treated with only base fungicides and insecticides, whereas the winter wheat varieties grown from seeds treated (coated) with the MON 201251 isolated strain showed a significant broad acre yield increase of 2.9 bu/acre.

TABLE 3

Wheat Broad Acre Yield Delta (bu/acre)

| Microbe | Spring Wheat | Winter Wheat |
|---|---|---|
| MON 202477 | −1.3 | 0.5 |
| MON 201251 | −0.7 | 2.9 |

While the present invention has been disclosed with reference to certain embodiments, it will be apparent that modifications and variations are possible without departing from the spirit and scope of the present invention as disclosed herein and as provided by the appended claims. Furthermore, it should be appreciated that all examples in the present disclosure, while illustrating embodiments of the invention, are provided as non-limiting examples and are, therefore, not to be taken as limiting the various aspects so illustrated. The present invention is intended to have the full scope defined by the present disclosure, the language of the following claims, and any equivalents thereof. Accordingly, the drawings and detailed description are to be regarded as illustrative and not as restrictive.

The invention claimed is:

1. A plant, plant part or plant seed associated with a composition comprising an isolated *Bacillus psychrosaccharolyticus* strain and an agriculturally acceptable carrier, wherein
   (a) the *Bacillus* strain has been deposited as ATCC accession number PTA-123720 or PTA-124246;
   (b) the *Bacillus* strain has a 16S rDNA sequence that is at least 99.7% identical to SEQ ID NO: 1 and/or 2, and wherein the *Bacillus* strain confers a positive agricultural trait or benefit to a crop plant when the crop plant is treated or associated with the *Bacillus* strain; or
   (c) the *Bacillus* strain has a genome sequence that at least 99.7% identical to the corresponding genome sequence of the *Bacillus psychrosaccharolyticus* strain deposited as ATCC accession number PTA-123720 or PTA-124246, and wherein the *Bacillus* strain confers a positive agricultural trait or benefit to a crop plant treated or associated with the *Bacillus* strain,
   wherein the *Bacillus* strain is heterologous with respect to the plant, plant part or plant seed;
   wherein the plant, plant part or plant seed is a cereal plant, cereal plant part, or cereal plant seed;
   wherein the composition is applied or coated on at least a portion of an outer surface of the plant, plant part or plant seed; and
   wherein the *Bacillus* strain has been freeze-dried or lyophilized.

2. The plant, plant part or plant seed of claim 1, wherein the plant, plant part or plant seed is transgenic.

3. The plant seed of claim 1, wherein
   (a) the plant seed is a monocotyledonous plant seed; or
   (b) the plant seed is a corn, wheat, rice, barley, oat, or sorghum plant seed.

4. A bag or container comprising the plant seed of claim 1.

5. The plant, plant part or plant seed of claim 1, wherein the composition further comprises a pesticidal agent, plant nutrient or fertilizer.

6. The plant, plant part or plant seed of claim 1, wherein
   (a) the composition is formulated as a solid, liquid or gel;
   (b) the composition is formulated as a powder, pellet or granules; or
   (c) the composition is formulated as an emulsion, colloid, suspension or solution.

7. The plant, plant part or plant seed of claim 1, wherein the composition further comprises one or more of a lipo-chitooligosaccharide (LCO), a chitooligosaccharide (CO), a LCO-producing bacteria or fungus, and a chitinous compound.

8. The plant, plant part or plant seed of claim 1, wherein the composition further comprises one or more of a flavonoid, humic acid, fulvic acid, jasmonic acid or derivatives thereof, linoleic acid or derivatives thereof, linolenic acid or derivatives thereof, karrikin, and gluconolactone.

9. The plant, plant part or plant seed of claim 1, wherein the *Bacillus* strain is present in the composition at a concentration of at least $10^3$ cfu per milliliter or gram.

10. The plant, plant part or plant seed of claim 1, wherein the composition comprises a pure or substantially pure population of the *Bacillus* strain.

11. The plant, plant part or plant seed of claim 1, wherein
  (a) the *Bacillus* strain has a 16S rDNA sequence that is at least 99.95% identical to SEO ID NO: 1 and/or 2;
  (b) the *Bacillus* strain has a 16S rDNA sequence that is 100% identical to SEQ ID NO: 1 or 2; or
  (c) the *Bacillus* strain has nitrate reduction activity.

12. The plant, plant part or plant seed of claim 1, wherein the agriculturally acceptable carrier confers at least one beneficial characteristic to the composition.

13. The plant, plant part or plant seed of claim 12, wherein the beneficial characteristic is improved efficacy, stability, wetting, flowability or coating onto the plant, plant part or plant seed relative to a control composition lacking the agriculturally acceptable carrier.

14. The plant, plant part or plant seed of claim 1, wherein
  (a) the agriculturally acceptable carrier comprises a wetting agent or dispersant;
  (b) the agriculturally acceptable carrier comprises a binder or adherent; or
  (c) the agriculturally acceptable carrier comprises an aqueous solvent and a non-aqueous co-solvent.

15. The plant, plant part or plant seed of claim 5, wherein
  (a) the pesticidal agent is one or more of a fungicide, herbicide, insecticide, miticide, acaricide, nematicide, or gastropodicide; or
  (b) the pesticidal agent is selected from the group consisting of ipconozole, metalaxyl, azoxystrobin, prothioconazole, metalaxyl, fluoxastrobin, clothianidin, *Bacillus firmus, Penicillium bilaiae, Trichoderma virens* and *Bacillus amyloliquefaciens.*

16. The plant, plant part or plant seed of claim 14, further defined as a monocot, corn, wheat, rice, barley, oat, or sorghum plant part or plant seed.

17. A kit comprising the plant seed according to claim 1.

* * * * *